(12) United States Patent
Houff

(10) Patent No.: US 11,241,264 B2
(45) Date of Patent: Feb. 8, 2022

(54) STERNUM FIXATION DEVICE AND METHOD

(71) Applicant: CircumFix Solutions, Inc., Piperton, TN (US)

(72) Inventor: Louis Houff, Piperton, TN (US)

(73) Assignee: CircumFix Solutions, Inc., Piperton, TN (US)

(*) Notice: Subject to any disclaimer, the term of this patent is extended or adjusted under 35 U.S.C. 154(b) by 311 days.

(21) Appl. No.: 16/208,707

(22) Filed: Dec. 4, 2018

(65) Prior Publication Data

US 2019/0099207 A1    Apr. 4, 2019

Related U.S. Application Data

(62) Division of application No. 14/178,107, filed on Feb. 11, 2014, now Pat. No. 10,154,864.

(60) Provisional application No. 61/801,005, filed on Mar. 15, 2013.

(51) Int. Cl.
| | | |
|---|---|---|
| *A61B 17/58* | (2006.01) | |
| *A61B 17/82* | (2006.01) | |
| *A61B 17/80* | (2006.01) | |
| *A61B 17/84* | (2006.01) | |

(52) U.S. Cl.
CPC ........ *A61B 17/823* (2013.01); *A61B 17/8004* (2013.01); *A61B 17/8061* (2013.01); *A61B 17/82* (2013.01); *A61B 17/842* (2013.01)

(58) Field of Classification Search
CPC ... A61B 17/8076; A61B 17/823; A61B 17/82; A61B 17/7059; A61B 17/8042; A61B 17/80; A61B 17/8004; A61B 17/8061; A61B 17/808; A61B 17/8085; A61B 17/809; A61B 17/842
USPC .............. 606/70–71, 280–299, 905–906
See application file for complete search history.

(56) References Cited

U.S. PATENT DOCUMENTS

| | | | |
|---|---|---|---|
| 1,950,799 | A | 3/1934 | Jones |
| 4,119,091 | A | 10/1978 | Partridge |
| 4,730,615 | A | 3/1988 | Sutherland et al. |
| 4,896,668 | A | 1/1990 | Popoff et al. |
| 5,139,498 | A | 8/1992 | Ley |
| 5,190,545 | A | 3/1993 | Corsi et al. |

(Continued)

FOREIGN PATENT DOCUMENTS

| | | |
|---|---|---|
| JP | S62270147 A | 11/1987 |
| JP | 2003515571 A1 | 5/2003 |

(Continued)

OTHER PUBLICATIONS

The United States Patent and Trademark Office; The International Search Report and the Written Opinion of the International Searching Authority, or the Declaration; International Search Report and the Written Opinion for PCT/US14/11187; dated Apr. 4, 2014; pp. 1-11; The United States Patent and Trademark Office as searching authority; U.S.

(Continued)

*Primary Examiner* — Jessica Weiss
(74) *Attorney, Agent, or Firm* — Waller Lansden Dortch & Davis, LLP; Matthew C. Cox

(57) ABSTRACT

An apparatus and technique for infernally securing a plurality of bone segments together. The device incorporates a plate-like structure stabilizing the fracture and integrated fasteners to attach straps circumscribing the bone segments.

9 Claims, 30 Drawing Sheets

(56) References Cited

U.S. PATENT DOCUMENTS

| | | | |
|---|---|---|---|
| 5,330,489 A | 7/1994 | Green et al. | |
| 5,702,399 A * | 12/1997 | Kilpela | A61B 17/82 |
| | | | 606/103 |
| 5,722,976 A | 3/1998 | Brown | |
| 5,941,881 A | 8/1999 | Barnes | |
| 6,387,099 B1 | 5/2002 | Lange et al. | |
| 7,033,377 B2 | 4/2006 | Miller, III | |
| 7,537,596 B2 | 5/2009 | Jensen | |
| 9,585,705 B2 * | 3/2017 | Koch | A61B 17/1604 |
| | | | 606/280 |
| 10,154,864 B2 * | 12/2018 | Houff | A61B 17/82 |
| | | | 606/74 |
| 2007/0038218 A1 | 2/2007 | Grevious | |
| 2007/0123883 A1 | 5/2007 | Ellis et al. | |
| 2008/0208205 A1 | 8/2008 | Kraemer | |
| 2009/0105717 A1 | 4/2009 | Bluechel | |
| 2009/0287215 A1 | 11/2009 | Fisher et al. | |
| 2010/0094294 A1 | 4/2010 | Gillard et al. | |
| 2010/0211075 A1 | 8/2010 | Stone | |
| 2011/0035008 A1 | 2/2011 | Williams | |
| 2011/0087295 A1 | 4/2011 | Kubiak et al. | |
| 2011/0106153 A1 | 5/2011 | Stone et al. | |
| 2011/0295257 A1 | 12/2011 | McClellan et al. | |
| 2012/0041441 A1 * | 2/2012 | Bernstein | A61B 17/823 |
| | | | 606/74 |
| 2012/0059424 A1 | 3/2012 | Epperly et al. | |
| 2012/0089193 A1 | 4/2012 | Stone et al. | |
| 2012/0221060 A1 | 8/2012 | Blain | |
| 2013/0165933 A1 | 6/2013 | Gephart | |
| 2013/0172944 A1 * | 7/2013 | Fritzinger | A61B 17/0401 |
| | | | 606/286 |
| 2013/0289564 A1 | 10/2013 | Bernstein et al. | |
| 2013/0296930 A1 | 11/2013 | Belson et al. | |
| 2014/0155895 A1 | 6/2014 | McClellan et al. | |
| 2014/0243905 A1 | 8/2014 | Cavallazzi et al. | |
| 2015/0045794 A1 | 2/2015 | Garcia et al. | |
| 2016/0000483 A1 | 1/2016 | Stone | |
| 2019/0099207 A1 | 4/2019 | Houff | |
| 2020/0078063 A1 | 3/2020 | Garcia et al. | |

FOREIGN PATENT DOCUMENTS

| | | |
|---|---|---|
| JP | 2005137757 A | 6/2005 |
| JP | 2010535553 A | 11/2010 |
| WO | 2009021876 A2 | 2/2009 |
| WO | 2012114360 A1 | 8/2012 |
| WO | 2013003719 A1 | 1/2013 |

OTHER PUBLICATIONS

The United States Patent and Trademark Office; The International Search Report and the Written Opinion of the International Searching Authority, or the Declaration; International Search Report and the Written Opinion for PCT/US14/015875; dated May 6, 2014; pp. 1-13; The United States Patent and Trademark Office as searching authority; U.S.

European Patent Office; Communication pursuant to Article 94(3) EPC; Examination Report; dated Oct. 25, 2016 pp. 1-5; European Patent Office; Germany.

* cited by examiner

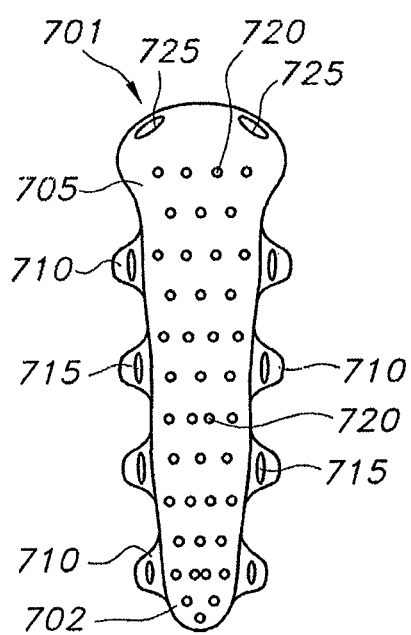 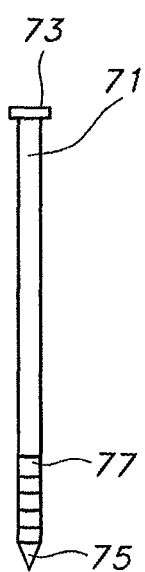 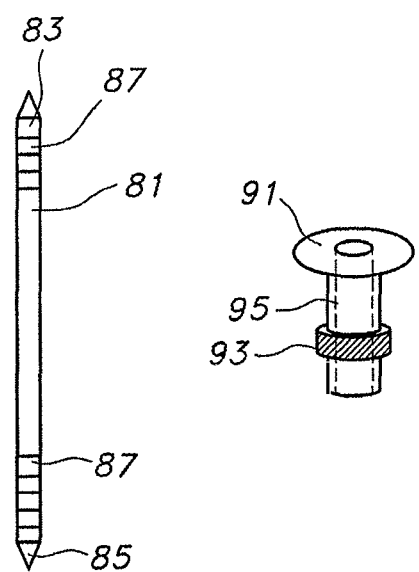
FIG. 8  FIG. 9  FIG. 10  FIG. 11

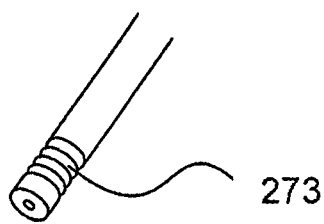 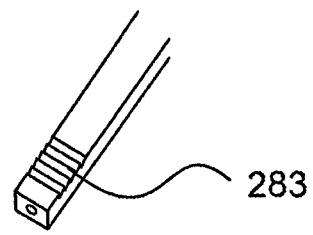
Fig. 21A  Fig. 21B
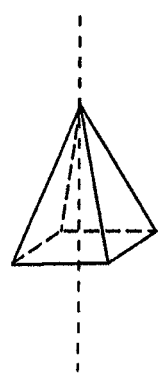 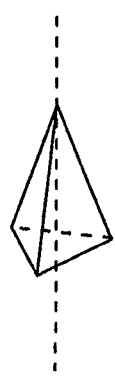 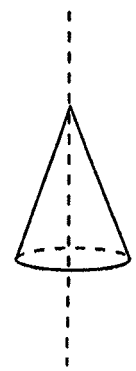
Fig. 22A  Fig. 22B  Fig. 22C

STERNUM FIXATION DEVICE AND METHOD

CROSS-REFERENCE TO RELATED APPLICATION

The present application is filed under 35 U.S.C. § 120 as a divisional application of U.S. Nonprovisional patent application Ser. No. 14/178,107, filed Feb. 11, 2014, which claims priority to United States Provisional Patent Application No. 61/801,005, filed on Mar. 15, 2013, the specifications of which are hereby incorporated in their entirety herein.

FIELD OF THE INVENTION

This invention relates to an implantable sternum fixation device to secure and aid in the healing of a surgically cut or fractured sternum.

BACKGROUND OF THE INVENTION

Over the last 30 years Open Reduction Internal Fixation (ORIF) with Rigid Internal Fixation (RIF) has become accepted as the standard of care for treating many types of fractures helping patients painlessly return to pre-injury function earlier and more reliably than conventional treatment methods such as casting, bracing, interosseous wiring and cerclage wiring. In addition, when properly applied RIF improves the reestablishment of pre-fracture anatomical bone alignment promoting more reliable infection free healing. Besides the proven benefits in trauma care, ORIF is an acceptable method of repositioning bones in elective procedures and repairing bones surgically cut or fractured when necessary to gain surgical access to perform a primary procedure. Such is the case in open-heart surgery where the sternum is surgically cut to gain access to cardiovascular structures contained within the chest wall. In such cases the sternum is surgically cut along the midline of the long axis of the bone separating the sternum and the associated rib cage in half sections left and right.

The standard method for reconstructing the surgically cut sternum is the placement of stainless steel wires circumferentially (cerclage) around the sternum segments and compressing together by twisting the wires tight to hold the surgically cut bone ends together approximating the pre-cut anatomical position of the sternum and chest wall. In most cases wire fixation has proven to be a successful and cost effective method of repairing the cut sternum with minimal reports of infection and non-union. The literature describes complication rates (infection and/or non-union) as high as 8%. Patients that incur complications, however, can endure significant pain and resolving their issues has proven difficult, time consuming, and expensive.

Patients with certain underlying health issues are predisposed to complications and a delayed healing response. For instance, perhaps most significantly, certain cardiovascular patients with multiple health issues including, as examples, COPD, diabetes, and/or suppressed immune response that may delay or prevent healing, exhibit a propensity for post-operative infection, hardware failure and/or nonunion of the sternum. Other factors, such as age, poor diet, smoking, alcohol abuse and/or drug use, can also adversely affect healing. Many of these patients exhibit diseased bone that is weak and may lack sufficient cortical density and thickness.

Over the years, numerous attempts have been made to improve a method for fixing the sternum, but most devices are designed to address the sternum after complications have arisen and are not intended to prevent complications by providing an improved primary solution. Furthermore, many of the commonly marketed products tend to be over engineered, complicated and time-consuming to implant. There are also a host of devices that do not appropriately address the complexities of the human anatomy and the demands such fixation must address in clinical application. Those devices tend to offer little to no benefit over wire fixation and may lead to unexpected and unintended complications beyond what is known from wire fixation.

The sternum is a flat bone with a thin cortex shell (dense outer bone layer). Cortical density and thickness are important factors with screw fixation techniques as they provide resistance against pullout when screws are tightened as purchase is achieved by the threads compacting and resting in bone. Cortical density and thickness are also important factors in cerclage wire fixation as stability relies on wires compressing directly against the cortex to maintain secure fixation.

An implant construct must provide and maintain sufficient stabilization for a duration long enough to allow bone healing to occur. If healing does not occur within an acceptable timeframe hardware loosening often leading to hardware failure becomes an increasing risk. This principle also applies to sternum fixation. In the patient population prone to delayed healing and increased risk of complication, cerclage wire fixation may be contraindicated. In such cases, fixation failure occurs due to broken or loosened wires. In some instances, such wire (loosen by cutting through the sternum cortex (commonly referred to as the "cheese grater effect"), which leads to mobility of the bone fragments, potential fracture of the sternum, and almost certain infection. Frequently when patients exhibit failed cerclage wire fixation, radical debridement of soft tissue and bone is necessary and subsequent reconstruction resembles a salvage procedure.

Coughing, which is a very common post-operative occurrence, especially with patients with COPD or pneumonia, generates high peak forces that act on the repaired sternum, thus increasing the incidence of failure of cerclage wire, as well.

Uncontrolled motion between two fractured bone fragments may also contribute to an increased incidence of infection. As such, the fixation construct chosen must control motion under functional loading conditions to create a favorable healing situation. Opinions have varied over the years as to how much rigidity is desirable in a fixation construct. Historically, it was considered a treatment goal to create a motion-free interface between two bone fragments which can be achieved by compressing the fractured or severed bone surfaces in direct opposition, eliminating all motion and encouraging direct healing without the formation of callus. However, it has now been realized, through the passage of time and the gaining of valuable experience in this area, that the need for extreme rigidity, and thus the elimination of all motion in this situation, is not necessary nor the prevention of callus formation. In essence, it has been found that fixation constructs that are substantially more rigid than the bones they are holding can lead to a condition known as stress shielding that fosters poor bone quality and strength giving rise to potential secondary complications including re-fracture. Load-sharing by implants is increasingly gaining favor as it is thought to promote healthier and stronger bone.

Another consideration is whether fixation implants can and should be left in the body long-term or permanently. There are many factors to consider such as patient age, the anatomical location of the implant, and the difficulty in removal. Generally, however, most surgeons prefer to leave fixation implants in vivo permanently and not perform a secondary procedure for removal whenever possible. Many cases of fixation implant removal result from patient complaints of discomfort, irritation, and palpability. An ideal implant design is one that can be left in the body permanently and causes little or no pain or discomfort to the patient during the healing phase and beyond.

The implant material is another major consideration in making the best implant fixation choice. It is vitally important (for clear reasons) that the implant be biologically stable and not cause irritation or another undesirable response while in the body. Furthermore, consideration should be given to an implant's potential effect on diagnostic, imaging, monitoring and other therapeutic technologies necessary to deliver post-operative patient care.

The speed and ease of installation are important considerations to make when choosing an implant fixation construct. Cardiovascular surgeons are not orthopedists and therefore not routinely familiar with drills, screwdrivers and other "bone carpentry" tools. Many sternum closure devices currently offered require such items as they are based on orthopedic plate and screw technology. These devices typically require multiple instruments to apply, have numerous individual component parts, and take an excessive amount of time to apply adding additional time, complexity and cost to the surgery.

The speed and ease of implant removal are also critical factors when choosing a fixation implant construct, especially in the case of a target sternum whereby emergency surgical re-access may be required should the patient incur a life-threatening health event necessitating surgical reentry of the chest wall. If a device requires special instruments to remove or has become biologically imbedded in the soft tissues and/or bone, valuable time can be lost dealing with locating removal instrumentation and exposing and removing the implants.

Additionally, the cost of an implant device construct must be reasonable and not add significantly to the overall cost of performing surgery. In the case of the sternum cerclage wire fixation, the material cost of surgical wire is insignificant. Plate and screw constructs for sternal closure range in price but easily can cost $3,000 to $5,000 per device. In addition, there are disposable components, such as drill bits, etc., that add to the cost and complexity of surgery. All known sternum-plating sets are configured as reusable trays containing an assortment of implants and reusable instruments requiring sterilization, cleaning, and restocking and storage between each use requiring additional costs and labor.

Typical sternal fixation devices include rigid-plate constructs with elaborate locking screws whereby the screws simultaneously thread into the plate and sternum which prevents the screws from becoming detached from the plate in the event they strip and become dislodged from the sternal bone. The instructions for use of such systems (such as available from Synthes and Biomet Microfixation) typically recommend a minimum of three plates and the placement of multiple screws to affix each plate to each independent bone segment. The plates are spaced and implanted along the anterior facing sternal surface midline straddling the saw cut with screws inserted into the sternum on both sides of the cut. Synthes offers a plate configuration that comprises of two halves joined together in the center with a removable u-shaped pin. If emergency re-access becomes necessary, the operator may remove the pins and separate the sternum and associated rib attachments left and right giving immediate access through the chest wall. However, uncoupling the plate assembly only mobilizes the underlying bone while the bone remains unhealed. If reentry is attempted after the soft tissue and/or bones have partially or fully united, simply removing the pins will not allow immediate re-access. In such instances, the bulky metal plates would interfere with a saw cut being made through the sternum in the conventional way without first removing the plates and screws, adding time and placing the patient at additional risk if access through the chest wall is urgently needed. Such screw-secured implants are also very time-consuming to implant and costly. Furthermore, their excessively rigid construction can result in stress shielding leading to poor bone quality and strength or delayed healing. Biomet Microfixation attempts to overcome the limitation of the Synthes design by making their plates cuttable in the center; however, a special cutting instrument is still required to cut and remove sections of implanted plates.

In another variation of a prior device, reduced stress shielding has been provided through the utilization of braided cables through sterna-positioned cannulated metallic grommets. Unfortunately, though, this alternative still requires excessive operating time and a skill-dependent implantation procedure. The cable is laced along the sternum like laces on a shoe and tightened with a special cable crimping instrument. The process for installation is too cumbersome and time consuming and getting the bone segments back into anatomical position has proven too difficult for widespread, reliable use.

Self locking fasteners, such as or similar to cable ties or zip ties placed circumferentially around the sternum through the intercostal spaces provide improved simplicity and potential time savings compared to wire fixation, but do not provide enough stability to adequately immobilize the bone segments sufficiently to achieve desirable and reliable healing for all patients. Like wire fixation, the zip tie fixation method disregards the significant forces loading on the sternum and is not an adequate solution for, in particular, at risk patients. Therefore, it appears to be a potentially more convenient way to achieve the same benefits of cerclage wiring.

Another available device designed for closing the chest wall and holding the sternum together following median sternotomy consists of a mechanical clamp that cleats around the sternum with extensions passing through the intercostal spaces. When used in series, these metallic clamps sold by KLS Martin compress the sternum together. The clamps are large, excessively rigid and frequently uncomfortable and irritating to the patient frequently necessitating post-operative removal, as well as comparatively costly. They also interfere with common imaging technologies including x-ray, CT and MRI.

There is a device available from Acute Innovations called Acutie that supposedly enhances the strength and stability of a cerclage wire construct. Surgical wire is passed around the sternum through the intercostal spaces and inserted through slots in a stainless steel plate, then tensioned and crimped. The method calls for multiple plates spaced along the anterior aspect of the sternum. The plates are substantially stronger than the bone and only prevent wire abrasion on a limited surface area of the sternum thus would seem to provide little benefit over wire fixation alone. The potential for wire to loosen, break and/or cut through bone is not entirely eliminated and might even be enhanced due to the plate stiffness transferring more load to the wire section in direct contact with bone.

Other identified competitive offerings tend to follow a plate and screw approach to fixing the sternum, typically with cuttable struts across the central section facilitating removal. None of them appear to offer significant benefits over each other and due to the significant forces that act on the sternum under extreme functional loading all present similar risks of complication due to inadequate load distribution and dissipation of forces acting on the chest wall.

A need thus exists for an inexpensive sternum fixation device that is easy to implant, achieves and maintains proper anatomical reduction, provides sufficient stiffness and stability to withstand the dynamic functional loads acting on the sternum under extreme physiological conditions, is load sharing by design to allow native bone to absorb limited forces to promote quality bone healing, is well tolerated by patients, poses no risk to the surrounding soft and hard tissues and other structures, can be left in the body long term allows quick access to the chest cavity by conventional methods, does not interfere with other diagnostic or therapeutic treatment during and after surgery, and can be quickly and easily removed should surgical reentry be necessary. To date, the sternum fixation industry has yet to provide such a beneficial alternative to the current devices described above.

BRIEF SUMMARY OF THE INVENTION

The invention disclosed involves a novel method referred herein as "circumfixation" device and method. This novel approach to fixation achieves a better fixation construct than previously available for a variety of clinical indications. In the case of sternum closure fixation, circumfixation device and method represents the perfect choice as it precisely addresses the prerequisites of sufficient rigidity, ease and speed of application and removal, biological stability, well tolerated, non-obstructive to other diagnostic and therapeutic technologies while remaining cost beneficial.

The inventive sternum circumfixation device and method can be best described as a type of internally placed splint comprising at least one specially designed plate-like body and a plurality of corresponding strap-like fastening members, herein also referred to as "locking fasteners." The body of the device, herein also referred to as "plate," is shaped to conform to a target patient's sternum and is configured to be placed along its anterior surface and secured in position by the use of zip tie-like fasteners that pass behind the sternum (the posterior side thereof) through the intercostal spaces and locked to the plate through special locking slots incorporated into the plate. The ideal material composition is a thermoplastic polymer such as polyether ether ketone (PEEK) because of its high strength and stiffness that can mimic human bone and its ability to be adapted to the irregular surface of the sternum and its high fatigue strength that permits prolonged load sharing common during a delayed healing response. The material's strength and stiffness allows the plate to be made in a low-profile configuration and to more closely replicate the strength and elasticity of the human sternum while being completely biologically compatible and well tolerated by the target patient. It has been realized that one of a large singular plate or singular plate having any number of correlated contours to the sternum shape and configuration allows for better anatomical restoration and is necessary to counteract the dynamic forces of tension, torsion and shear acting on the sternum, especially those acting along the forward or anterior facing surface of the sternum. The use of fasteners instead of screws or wires creates a more reliable fixation construct, and together with the plate they allow for load sharing and promote micro movement in the healing zone thought beneficial to promoting healthy healing of bone. In addition, fasteners can be applied quickly with minimal instrumentation and easily removed with common surgical scissors. Furthermore, whereas screws rely on healthy and dense bone for their threads to maintain grip and sternum bone has been shown to have poor cortical density and thickness that may not be sufficient to prevent screw strip out or wire cut out under the extreme loads common to the sternum during normal physiological function, the inventive devices places the loading over a larger surface area of cortical bone mass. Thus, the important considerations are the shape of the plate and the capability thereof of relating to the sternum sufficiently in shape to accord a comfortable and capable protective shield in combination with a strong, yet comfortable attachment component that runs along the posterior surface of the subject sternum and connects to both ends of the plate around a single intercostal space. The utilization of easily manipulated connection devices to reliably attach the attachment component on demand, and that also remains reliably in place within the structure of the plate for an undetermined period of time after implantation without exhibiting any appreciable loss of connection strength, additionally provides a highly desirable repair mechanism in this area.

Circumfixation provides the additional advantage of providing a biomechanical and biological approach to bone healing. It is appropriately termed "biomechanical" because this method considers not just the forces acting on the bone but the fundamental purpose of the bone itself. The fixation allows the bone to function in the manner it was intended while maintaining it sufficiently stable to achieve desirable and predictable healing. The term "biologic" applies because it mimics the strength, stiffness, and elasticity of the target bone while allowing the body's natural healing abilities to take effect. While spanning the sternum, the circumfixator plate rests on torsion rails or "piers" that add stiffness and minimize direct contact with the bone surface and thus which promotes the free flow of fluids and cellular activity at the healing site beneath the plate. Furthermore, the inert nature of the implant does not retard or interfere with desirable healing. It also avoids unnecessary trauma to bone that results from drilling and placing foreign bodies therein (such as screws and/or cables, as non-limiting examples). The sternum circumfixation construct applies desirable compression along the entire bone fragment interface which enhances healing while controlling movement and the range of dynamic forces acting on but not eliminating micromotion thought to be beneficial to the healing process. The splinting nature of the circumfixation construct promotes load sharing of extreme forces along the entire geometry of the plate in a similar way as exhibited by a healthy uncut or non-fractured bone (sternum). This action thus shields and protects the underlying bone from overloading while allowing some loading to transfer to the bone thought to be the ideal scenario for promoting the healthy healing of bone.

The sternum circumfixation construct is also safe and well tolerated by target patients. Unlike plates, screws, and/or clamps, there are no sharp edges or pointed tips that could seriously harm patients if they were to fall or suffer trauma to the sternum region either during the healing phase or after healing is complete. This new device thus also avoids the overly rigid metallic constructs that create stress risers in the surrounding bone. Overall, then, the inventive device further reduces the likelihood of secondary bone fractures that can occur as a result of overloading at the location of the stress riser. As mentioned earlier, many cardiothoracic patients have co-morbidities making them predisposed to infection, to delayed healing, and to poor bone quality and blood perfusion. For these high-risk patients especially, sternum circumfixation is a superior choice as a short term, long term, or permanent implantation period. The flush smooth surface of the sternum circumfixator and fasteners causes no irritation to the surrounding tissues and bone. The lack of metallic components, which are required of all known prior sternum repair devices with the exception of zip tie fasteners, also reduces the patient's sensitivity to cold temperatures, eliminates the potential of complications due to metal sensitivity and will not interfere with imaging and other diagnostic and therapeutic treatments. Furthermore, some patients who undergo open chest procedures may later require cardiopulmonary resuscitation (CPR) and the presence of a circumfixator would not interfere with performing such a procedure whereas metallic devices could make such a procedure difficult or impossible to perform and lead to other unintended consequences such as implant loosening or breakage, infection and/or bone fracture.

Accordingly, the invention thus encompasses herein a sternal splint to promote healing and protection of a person's sternal anatomy subsequent to a sternotomy, wherein said sternal body includes a sternum bone having an upper surface and underside sternal bone and a plurality of intercostal spaces between said person's ribs, wherein said splint is a singular plate having front and back ends construct spanning at least a portion of said upper surface and secured thereto with at least one locking fastener passing through said at least one intercostal space with attachment at both said front and back ends of said plate. Such a configuration may include a single plate that covers a portion of said sternum such that more than one fastener is utilized and said fasteners pass through more than one intercostal space between said person's ribs. Additionally, more than one such plate may be utilized at a time spaced accordingly along said person's sternal body. Such a plate (or plates) and fastener (or fasteners) promote weight load bearing to the upper surface of the sternal body as well as stress load dissipation across the plate entirety and underlying sternal bone to, again, provide a suitable healing situation after a sternotomy. Another manner of describing such an inventive device is as a bone plate containing at least locking mechanism connecting said plate with at least one independently placed locking fastener, wherein said at least one locking fastener and said plate form an implantable bone splint (to compress bone fragments together, for example) and wherein each of said at least one independent locking fasteners is adjustable for different tensioning levels.

In greater detail, then, one possible embodiment for this invention is an internal bone splint comprising: an elongated plate having a height greater than a width, said plate having a right side, a left side, a top, a bottom, front, a back; a plurality of apertures positioned within said elongated plate, extending through from said front side to said back side; a plurality of fastener straps configured to engage said apertures; and a plurality of self-locking mechanisms whereas each self locking mechanism is configured to allow a said fastener strap to pass through a said aperture when said fastener strap is passed from said back to said front direction, but resist a said fastener strap from passing through said aperture from said front to said back direction; wherein said back of said elongated plate includes protruding torsion rails. Additionally, the inventive device encompasses the same bone splint wherein said plate possesses a plurality of protrusions along said right and left sides, wherein each said aperture is positioned within a protrusion. The inventive device may further comprise a cannulated tensioning handle configured to receive a said fastener providing the operator a simple and convenient means of tensioning locking fasteners attached to the plate.

Alternatively, the invention may encompass an internal bone splint comprising: a first elongated plate and a second elongated plate, each plate having a height greater than a width, said plate having a right side, a left side, a top, a bottom, front, a back; a plurality of apertures positioned within said first elongated plate, extending through from said front side to said back side; a plurality of fastener straps configured to engage said apertures, said fastener straps attached at one end to said second plate; and a plurality of self-locking mechanisms whereas each self locking mechanism is configured to allow a said fastener strap to pass through a said aperture when said fastener strap is passed from said back to said front direction, but resist a said fastener strap from passing through said aperture from said front to said back direction; wherein said back of said elongated plate includes protruding torsion rails.

As another alternative, the invention may encompass a internal bone splint comprising a rigid or semi-rigid plate having a right side, a left side, a top, a bottom, a front, and a back; at least one aperture positioned within said elongated plate along either said right or said left side and extending through from said front side to said back side; at least one fastener strap configured to engage said at least one aperture; and at least one locking mechanism present adjacent to said aperture, wherein each locking mechanism is configured to allow said at least one fastener strap to pass through said at least one aperture when said at least one fastener strap is passed from said back of said plate to said front direction, but configured simultaneously to resist said at least one fastener strap from passing through said aperture from said front to said back direction; and wherein said strap is retained on the opposite side of said aperture by a stationary retention component. Furthermore, such a structure may also include a configuration wherein said plate includes at least one protrusions along said right and left sides, wherein each of said at least one aperture is positioned within said at least one protrusion, and wherein each aperture includes at least one fastener and at least one locking mechanism.

Also encompassed herein is a self locking fastener having a channel extending the length of said fastener through which a guide wire may pass, wherein said guide wire has a first end and a second end. The fastener may further comprise a handle, said handle attached to said second end of said wire.

Further encompassed within this invention is a method of internally bracing two portions of a sternum of a patient after a sternotomy comprising: placing a plurality of self locking fastener strap around the posterior of said sternum; placing a plate upon the anterior surface of said sternum, said plate having a plurality of apertures configured to allow the passing of a said self locking fastener strap in a one direction but resist the passing of a said self locking fastener in an opposite direction; passing each free end of each said fastener strap through a said aperture; placing a cannulated tensioning handle on a said free end of a said fastener strap; tightening said fastener strap to a desired tension; and cutting each said free end of each said fastener strap flush with said plate.

Thus, overall, the invention may also encompass a method of internally bracing two portions of a sternum of a patient after a sternotomy utilizing any of the above-describing and herein further described structures for such effect. As such, the inventive device may permit a suitable protective/healing method for a target patient by providing the inventive to a splint to the sternum of such a patient and utilizing the inventive fasteners described above to secure the splint around the subject sternum.

The invention will be further and more succinctly described below.

BRIEF DESCRIPTION OF THE DRAWINGS

FIG. 8 shows a front view of an embodiment of the invention.

FIG. 9 shows a single ended locking fastener of an embodiment of the invention.

FIG. 10 shows a double ended locking fastener of an embodiment of the invention.

FIG. 11 shows a cannulated tensioning handle of an embodiment of the invention.

FIG. 21A shows a perspective view of an embodiment of the locking fastener having a round profile.

FIG. 21B shows a perspective view of an embodiment of the locking fastener having a rectangular profile.

FIG. 22A shows a perspective view of the end of the locking fastener having a square pyramid shape.

FIG. 22B shows a perspective view of the end of the locking fastener having a triangular pyramid shape.

FIG. 22C shows a perspective view of the end of the locking fastener having a conical shape.

DETAILED DESCRIPTION OF THE DRAWINGS AND PREFERRED EMBODIMENTS OF THE INVENTION

Figure 1:
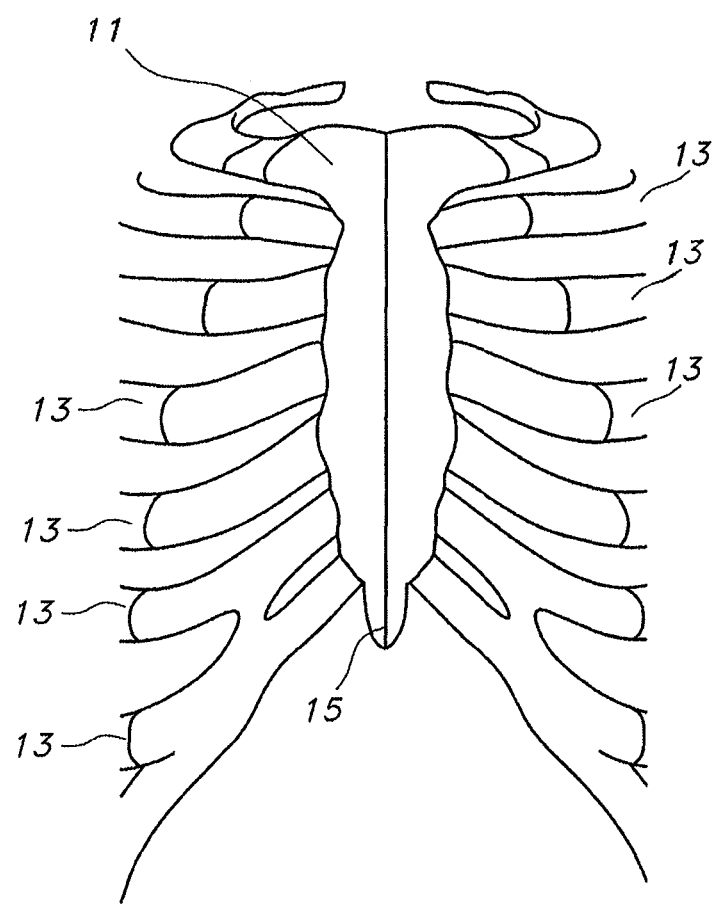
FIG. 1 is a front view of a sternum having a longitudinal cut.

The plate and fastener assembly must be sufficiently strong to withstand the biomechanical forces typical under normal and severe functional loading conditions. In the preferred embodiment, the implant material would be biocompatible, light weight, radiolucent and easily removable should emergent surgical re-entry through the chest wall be necessary. An ideal method of removal would be the ability to release the fixation with a common pair of surgical scissors by cutting through the fasteners allowing the plate and fasteners to be quickly and easily removed.

The purpose of this invention is to provide an improved implantable medical device and technique to repair and heal a surgically cut or fractured sternum and surrounding soft tissues with the goal to restore preoperative anatomical form and function and bony union though healing. The plate is thought to be semi-rigid allowing for flexing of the thorax during breathing, coughing and other physiological movements while maintaining anatomical positioning of the bony fragments during the healing phase. The device assembly is intended to be easily applied and removed if emergent re-access is indicated. The device is intended to reduce post-operative pain and allow early post operative mobilization of the patient which could lead to earlier rehabilitation and discharge, while reducing the potential for infection and the contraction of hospital acquired pathogens. The device is intended to be biocompatible allowing it to remain in the body permanently. The device is intended to be inert and radiolucent causing no interference with any testing, diagnostic or imaging technology applied to the patient postoperatively.

Many cardiac surgical procedures require passage through the chest wall to access the vital organs contained in the inner cavity. Surgical access is typically gained by cutting the sternum in half with a surgical saw along its long access (median sternotomy) allowing the separation of the chest wall and rig cage left and right.

A sternum closure device is designed to reduce and maintain the chest wall in anatomical position following open chest procedures in which a median sternotomy was performed.

Additionally, the proposed invention could be designed to elute therapeutic agents such as antimicrobials and/or bone healing agents like stem cells or BMPs. Alternatively, the device could be coated with said agents to promote infection free healing. The device could also be imbedded with smart technology to perform various diagnostic and/or clinical tasks or provide dockage for other implantable technologies. One example is the potential to embed an implantable bone stimulation capability to aid and assist bone healing.

While Circumfixation is primarily intended for the purpose of assisting in the healing of surgically cut and fractured bone, it could also be a valuable method for surgically implanting and hosting a range of undefined therapeutic and diagnostic technologies and agents unassociated with fracture repair that might benefit from in vivo delivery in anatomical locations not limited to the sternum.

The invention comprises a rigid or semi-rigid plate in the general shape of the human sternum that is placed over the sternum for the purpose of splinting the sternum into position for healing following a surgical cut to the sternum separating it into left and right halves longitudinally technically described as sternotomy. The device might also be applied to secure the sternum in position following traumatic injury resulting in fracture. The plate has spaced slots along the lateral edges of the plate to accommodate the placement of fastener straps that are passed behind the sternum and threaded through opposing slots. Some or all of the slots can be configured with a locking mechanism that allows the fasteners to be affixed to the plate when tensioned. The slots are spaced to overlay the gaps between ribs known as intercostal spaces allowing for the fasteners and plate to circumferentially surround the sternum and hold it in secure position to promote reduced pain or pain free bone and soft tissue healing mitigating many potential complications observed with conventional methods.

The plate might also be configured with a capability to deliver therapeutic agents such as antibiotics, pain control, cancer treatment, bone healing growth factors such as stem cells or BMPs, etc. The plate might also be coated with antibiotics or bone healing compounds and agents.

Circumfixation could have applications in rib fracture fixation, clavicle fracture fixation, scapula fracture fixation, proximal and distal femur fixation, proximal and distal tibia fixation, fibula fixation, proximal and distal humerus fixation, proximal and distal radius and ulna fixation, wrist bracing and/or reconstruction, ankle bracing and/or reconstruction, spinal bracing and/or reconstruction, pediatric fracture fixation, peri-prosthetic fracture management and fixation, veterinary fracture fixation and possibly other unidentified applications. The invention comprises of a plate contoured to lie passively against the forward facing aspect of the human sternum when placed directly on the sternum's irregular surface, zip tie-like fasteners secure around the sternum, securing the plate to the sternum. Attachable cannulated handles facilitate manipulating and tensioning the fasteners. The sternum plate could be made of a biocompatible thermoplastic polymer material like PEEK, PEAK, PAEK, UHMWPE, Silicone, ULTEM, RADEL, PPO, PPS, Nitinol, Stainless Steel, Titanium alloy, oxidized zirconium, ceramic, cobalt chrome, resorbable polymers, carbon fiber, carbon fiber reinforced PEEK or collagen. The sternum plate should be thin (preferably 1-10 mm thick) slightly tapered in the relative shape of a human sternum, slightly parabolic or possibly rectangular in the general dimensions to resemble the human sternum. The plate should have a series of spaced or contiguous slots (holes) placed near the outer or distal edges in direct opposition to each other along the long axis of the plate. The purpose of the slots is to provide a docking port for the fastener ends to attach to the plate. The slots contain locking mechanisms that secure around the notched or ribbed profile of the fastener ends when they are inserted and advanced through the slots. The slots could also be spaced for the purpose of aligning them with the intercostal spaces (the space between ribs at the juncture where they meet the sternum). In addition, the slots could be placed on winged tabs incorporated into the plate design that extend slightly past the sternum and over the intercostal spaces allowing the easy passage of fasteners around the posterior aspect of the sternum connecting to the plate on both sides through the slots. The winged tabs might be bendable to adapt to the surface of the bony anatomy when the fasteners are tensioned. In an alternative embodiment, the plate is porous having perforated holes to allow body fluids to pass through and around the plate.

When secured in place the device assembly supports and holds the surgically cut bones and their attachments in anatomical approximation effectively holding closed the chest wall by compressing together along the cut or fractured bone surfaces promoting reduced pain or pain free healing of the sternum and surrounding tissues while at the same time allowing the flexibility for the chest cavity to expand and contract during breathing, coughing and other physiological loading. The fasteners interact with the sternum plate by attaching to it through the slots and compressing the device assembly around the bony fragments when tensioned bringing the surgically cut bone ends into direct contact to promote biological healing with bony union.

Without any intention of setting limitations on the breadth of the invention described herein and encompassed within the accompanying claims, herein provided are descriptions of drawings of the non-limiting preferred embodiments of the inventive device.

FIG. 1 shows a frontal view of the sternum 11 and a plurality of ribs 13. Typically a cut 15 is made in the sagittal plane along the midline of the sternum 11 longitudinally allowing the separation of the sternum 11 and rib cage attachments left and right. The device is to be implanted at the time of closure allowing the separated segments of the sternum 11 to be anatomically re-approximated and compressed together to promote bony union and healing of the surrounding soft tissues while reducing or eliminating pain, infection and potential of non-union. The invention could also be used to repair and reconstruct the chest wall following traumatic injury sustained as a result of fracture(s) to the relative bony structures. This FIG. 1 thus merely shows the prior art situation of a surgically cut sternum in need of some type of connection to promote healing.

Figure 2:
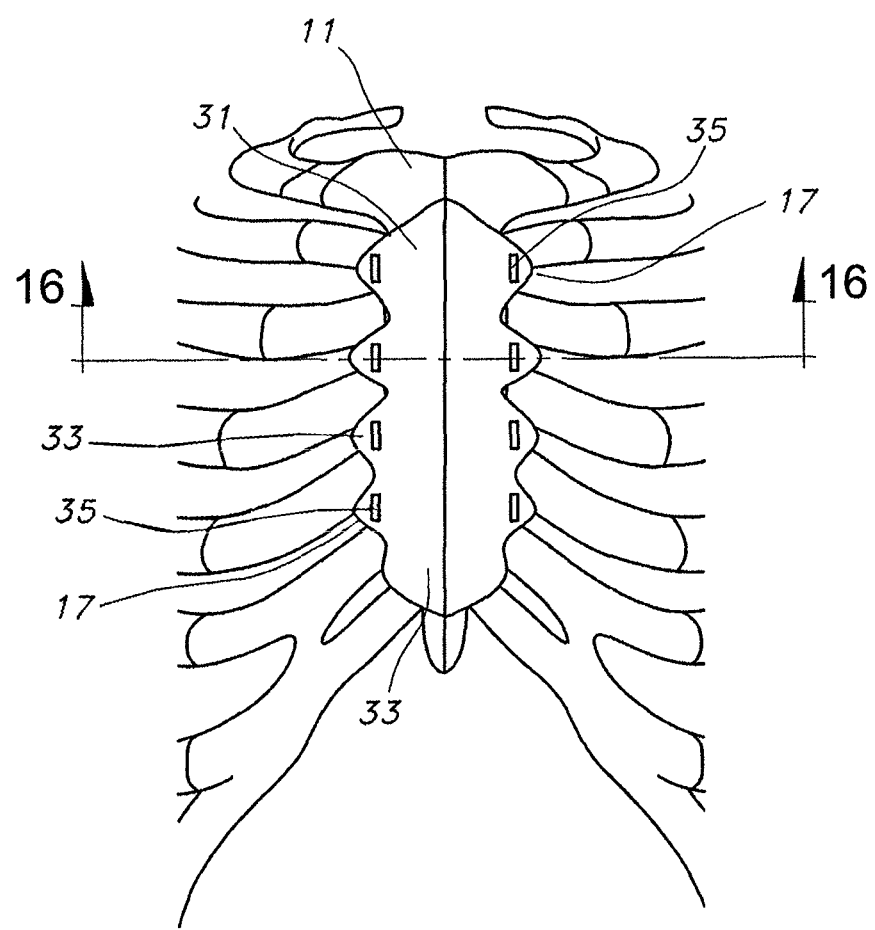
FIG. 2 is a front view of a first embodiment of the invention.

FIG. 2 thus shows a first embodiment of the invention 31 comprises a plate 33 that is placed over the sternum 11 and is secured in position in a splint-like fashion with a plurality of self locking fasteners, such as zip ties, passed behind the sternum 11 through the intercostal spaces 17 and attached and secured to the plate 33 through corresponding slots (also referred herein as holes or apertures) 35 in the plate 33 with some or all incorporating a locking mechanism which grips and locks around the notched or ribbed textured surface of the fastener ends. When sufficiently tightened the plate and fastener assembly compresses the plate, fasteners and the bony fragments snugly together in anatomical position reducing pain and promoting postoperative healing of the bone and surrounding tissues. As noted above, this fixation modality is described herein as "circumfixation."

Figures 3A, 3B:
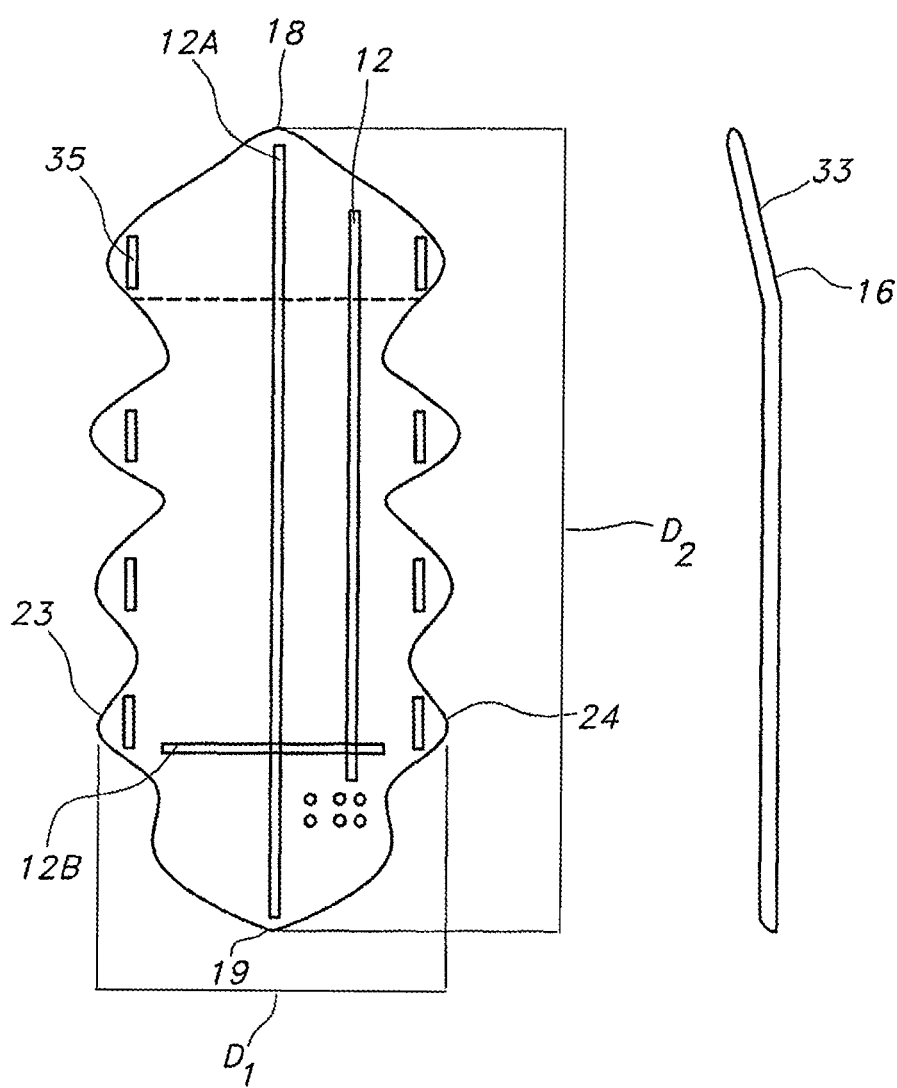
FIG. 3A is a rear view of the invention showing partially formed torsion rails and perforations.
FIG. 3B shows a right side view of the invention of FIG. 3A.

FIG. 3A shows a rear view of the first embodiment of the invention, showing a plurality of torsion rails which stiffen the plate while providing reduced surface area contact with the underlying bone.

FIG. 3B shows a side view of the first embodiment of the invention.

Figure 4:
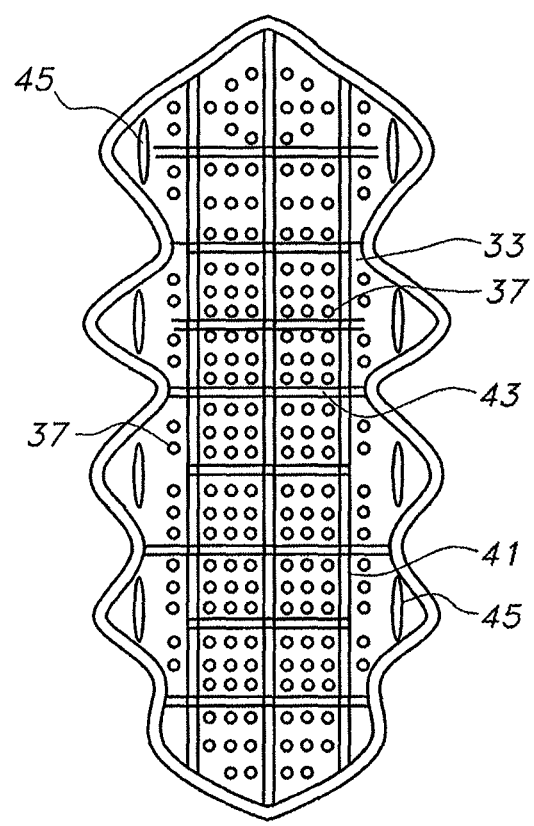
FIG. 4 shows a rear view of the invention showing of FIG. 3A.

FIG. 4 shows a rear view of the first embodiment of the invention 31, showing a plurality of perforations 37 though the plate body 33, torsion rails 41, 43 and apertures 45 through which fasteners may pass.

Figure 5:
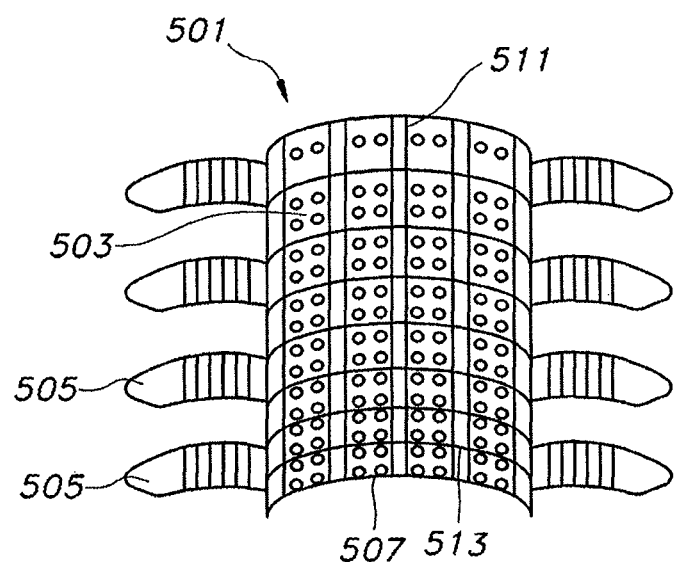
FIG. 5 shows a rear view of the male plate portion of a second embodiment of the invention.
Figure 6:
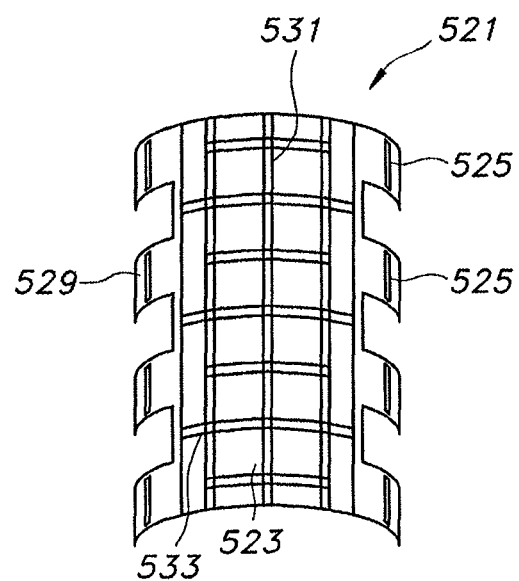
FIG. 6 shows a rear view of the female plate portion of a second embodiment of the invention.

FIGS. 5 and 6 show a dual plate embodiment having a male plate 501 and a female plate 521. The male construct 501 possesses a plurality of fastener straps 505 extending from the plate body 503. In this particular embodiment, the male plate body 503 possesses a plurality of apertures 507 allowing the passage of fluids through the plate. The plate body 503 also possesses a plurality of elongated protrusions or "torsion rails" 511 running up and down as well as a plurality of torsion rails 513 running across the body 503. The female construct 521 possesses a plurality of torsion rails 533 and 531 which increase the plate body 523 rigidity and reduce the total contact surface area with the tissue being secured by the plate. A plurality of apertures 525, each possessing a self locking mechanism receive the male fasteners 505 of the male construct plate construct 501. The apertures 525 are be positioned, preferably, out on protruding sections or wings 529 of the body 523.

This type of circumfixation is referred to as circumfixation method "type B." Whereas the first embodiment and method described the use of a plate and multiple independent locking fasteners to create a fixation construct, the "type B" method does not employ independent locking fasteners, rather, the fastening feature is incorporated into the plate body geometry 503, 523 resembling phalanges extending from the body of the plate. Locking phalanges 505 extending from the body of the plate herein referred to as "male" plate body are joined to a second plate body with corresponding locking slots 525 designed to accept and secure around the profile of the locking phalange fastener ends herein referred to as "female" plate body when they are inserted through the locking corresponding locking slots. The size, shape, thickness, strength, stiffness and material composition of "type B" circumfixator plate bodies and the quantity, size, strength and flexibility of the locking phalanges and receptor locking slots will vary depending on a number of factors including the intended purpose, anatomical location; the size shape, quality and quantity of the bone, bone segments and fragments, etc.

Such a construct might be favorable for fixing or splinting bones round or tubular in shape, including ribs, the spine, femur, tibia, fibula, radius, ulna, humerus, carpels, metacarpals, phalanges, tarsals, metatarsals, clavical, and the like. Such a construct might also prove ideal for fixing or splinting peri-prosthetic fractures, various pediatric fractures and osteotomies, and fixing and/or splinting in or over joint areas including the hip, knee, ankle, wrist, elbow, shoulder, spine, fingers and toes.

Figure 7:
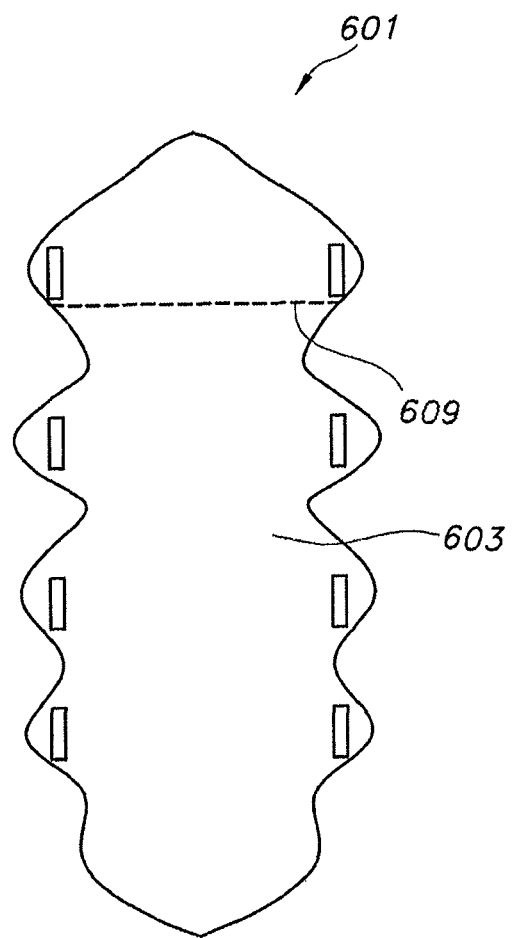
FIG. 7 shows a front view of the invention having a contour transition on its underlying surface to conform at the sternal angle being the junction of the sternal body and the manubrium.

FIG. 7 shows another embodiment 601 of the invention possessing no torsion rails. This version possesses a thinned horizontal section 609 allowing flexion of the sternum plate 603 along the sternum and manubrium border.

Fasteners 71, 83 could have single ended locking capability as shown in FIG. 9 or a double ended locking capability as shown in FIG. 10. Likewise plate slots could be locking or passive (non-locking). Under such a scenario whereby the slots incorporated into the plate are passive and do not contain the locking mechanism necessary to lock around the fastener profile, a special locking nut or "donut" could be utilized to achieve the same purpose. A locking nut is slipped over a fastener that has been inserted through a passive plate slot and slipped down around the fastener profile until it meets the plate surface at the junction where the fastener 711 and the passive plate slot 703 intersect. The locking nut would contain a locking mechanism allowing it to grip around the profile of the fastener and prevent the fastener from backing through the slot. The fastener could be tensioned by advancing it through the slot and locking nut allowing for a snug and secure closure. After final tensioning, the excess fastener body would be trimmed and removed just above the top of the locking fastener where the fastener body exits the locking nut.

A single-ended fastener could have a head 73 at one end that stops and rests flush when it meets the surface of the plate after it is threaded through a non-locking slot and tensioned when the locking end of the fastener is passed through the corresponding or opposing locking slot on the contralateral side of the plate and thereafter tensioned. The distal end 75 of the fastener will lock after threading through the distal plate slot and thereafter tensioned. A double-ended fastener 81, whereby both ends offer the capacity to be simultaneously tensioned and locked through opposing plate locking slots, could be beneficial to achieving even tensioning of an implant construct. This would apply to plate slots containing a locking mechanism or passive slots and the use of locking nuts. The surface geometry of the fasteners could be square, as shown in FIG. 21A, rectangular (flat), or rounded as shown in FIG. 21B. A rounded or hexagonal surface may possess less of a potential to irritate the bone and adjacent soft tissues under tension and physiological loading. All potential fastener geometries are better able to evenly distribute their forces across a larger surface area compared to wire which should reduce the potential for irritation and infection. Fasteners may also be cannulated allowing the insertion of a guide wire through their core to facilitate their passage through soft tissues, muscle and cartilage encountered around the sternum at the time of placement. Alternatively, fasteners might incorporate a cardiac needle affixed on one end to aid in their passage through soft tissue, muscle, and cartilage found around the sternum. After tunneling through the soft tissue, muscle and/or cartilage the cardiac needle can be severed from the fastener and discarded.

Cannulated handles 91 as shown in FIG. 11 could be temporarily attached to the fastener ends 75, 83 or 85 once they are threaded through opposing plate slots giving the operator a means of tensioning the fasteners in position by pulling on the handles. Cannulated handles 91 could be made of metal or plastic and might have a threaded nut/ring 93 around their barrel 95 that when tightened reduces the cannulation aperture allowing them to attach to fastener ends for tensioning and manipulation. Upon un-tightening (or loosening) of the threaded nut/ring the handle can be easily removed. Cannulated handles could be used on single- or double-ended locking fasteners also with or without the use of locking nuts. By pulling on cannulated handles attached to the fastener ends the device assembly surrounding, the bone fragments can be manipulated allowing the bone fragments to be reduced into anatomical position and securing the device assembly in position by compressing the plate and fasteners around the bony fragments.

The plate and fastener assembly must be sufficiently strong to withstand the biomechanical forces typical under normal and severe functional loading conditions. In the preferred embodiment, the implant material would be biocompatible, light-weight, radiolucent and easily removable should emergency surgical re-entry through the chest wall be necessary. An ideal method of removal would be the ability to release the fixation with a common pair of surgical scissors by cutting through the fasteners allowing the plate and fasteners to be quickly and easily removed.

Figure 12:
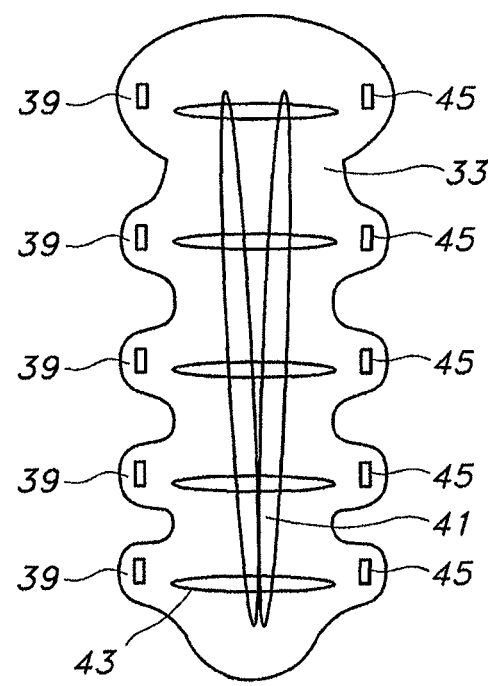
FIG. 12 shows a rear view of an embodiment of the invention.

As shown in FIG. 12, the plate 33 may be configured with rigid or bendable flaps or wings 39 with the slots located within to facilitate simplified placement of the fasteners. Due to anatomical differences of different statured patients it might be necessary to offer multiple sizes of plates to properly conform to the variable anatomy.

Preferably the fasteners have a rack of ridges resembling zip-ties. In the preferred embodiment the fasteners could lock through corresponding "female" slots incorporated in the plates 33 each slot containing a locking mechanism that prevent the fasteners from backing out after the ends are threaded through slots. Alternatively, fasteners could be secured with locking nuts that each contain a locking mechanism and secure the fasteners in position when advanced along the outer profile of fasteners once they have been passed through passive or non-locking plate slots and firmly pressed up against the plate slot interface restricting the fastener from backing through the plate slot. There are two major types of fasteners: single ended locking and double-ended locking. FIG. 9 shows the single ended locking fastener (SELF) 71 which has a head 73 on one end that prevents it from pulling through a non-locking slot and has a textured surface 77 on the opposite end 75 that allows it to mesh with the locking mechanism contained in the corresponding locking slot preventing it from backing out when tensioned. The second type of fastener would be the double ended locking fastener (DELF) 81 whereby both ends of the fastener 83, 85 can be locked through slots containing locking mechanisms. In an alternative embodiment of either type of fastener, the fastener has a cardiac needle fused to one of the male ends through a molded in process or suture tie. The use of cardiac needles will allow the operator to easily pass the attached fasteners through the soft tissue, muscle and cartilage adjacent to and surrounding the sternum. The fasteners are placed behind the sternum and emerge through the intercostal spaces on both sides of the sternum and attached to the plate by threading through the slots. Before or after the male end is threaded through the female slot with locking mechanism the cardiac needle can be removed from the end and the fastener can be tensioned pulling the sternum fragments closed. Once the chest wall is sufficiently closed the excess fastener end can be trimmed back and removed leaving the fastener flush at the surface of the locking slot. Alternatively, a special cannulated awl could be used to tunnel under the sternum easing the passage of fasteners without the use of cardiac needles.

The cannulated tensioning handle can be used to tension the fasteners to enable closure of the open sternum. This is done by engaging the end of the fasteners with the handle so that the handles can be pulled with human power to provide tension on the fasteners pulling against the strut plate and close the sternum. After tensioning the handles can be released from the fasteners and the handles can be disposed.

The sternum plate covers the sternum body and manubrium and is affixed to the bony anatomy with zip tie-like strap fasteners that pass behind the sternum and lock to or through the plate that is placed on the forward facing aspect of the sternum and manubrium. When secured in place the device assembly supports and holds the surgically cut bones and their attachments in anatomical approximation effectively holding close the chest wall by compressing together along the cut or fractured bone surfaces promoting reduced pain or pain free healing of the sternum and surrounding tissues while at the same time allowing the flexibility for the chest cavity to expand and contract during breathing, coughing and other physiological loading. The fasteners interact with the sternum plate by attaching to it through the slots and compressing the device assembly around the bony fragments when tensioned bringing the surgically cut bone ends into direct contact to promote biological healing with bony union.

Figure 13:
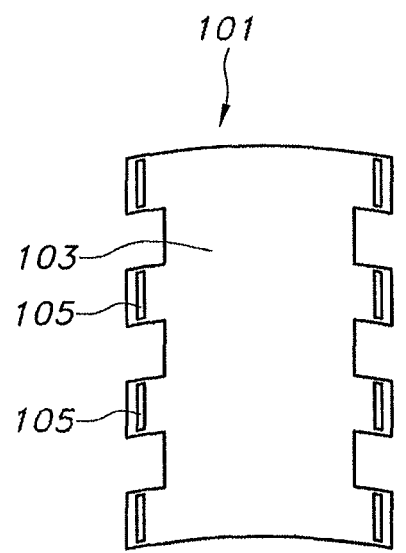
FIG. 13 shows a female portion of an two plate embodiment of the invention.
Figure 14:
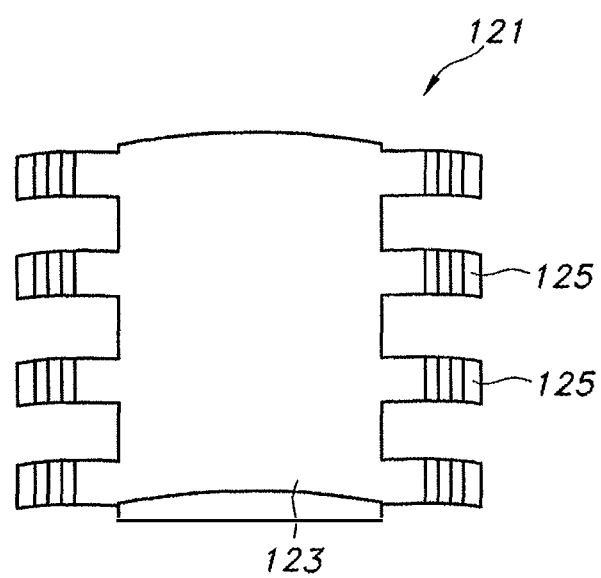
FIG. 14 shows a male portion of an two plate embodiment of the invention.

FIGS. 13 and 14 show a dual plate embodiment of the invention where a female circumfixation plate 101 and a male circumfixation plate 121 may be joined and fastened around a bone or bone fragments to aid in the stabilization and union of the bone. The female plate 101 possesses a plurality of apertures 103, each aperture having a self locking fastener mechanism. The male plate 121 possesses a plurality of fastener straps 125 built into and extending out from the plate body 123. The male plate 121 may be positioned upon one side of the bone, or bone fracture, while the female plate 101 is positioned upon the opposite side. The fastener ends 125 are fed through the apertures 105 and tightened to secure the plates 101, 121 together. The excess fastener end 125 may then be removed so the remaining end of the implanted fastener is flush with the female plate body 103.

Figure 15:
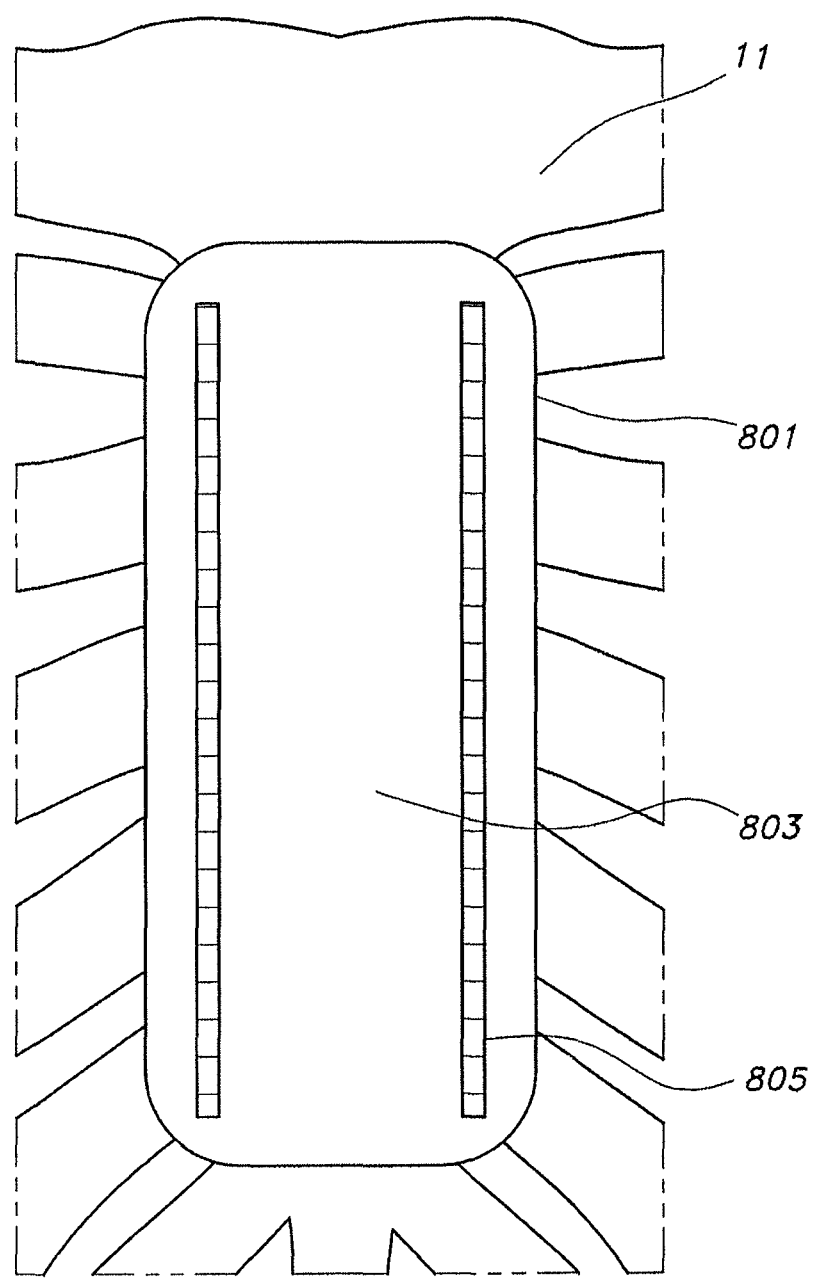
FIG. 15 shows an embodiment of the invention having a plurality of apertures spaced in close proximity along each side of the plate.

FIG. 15 shows the sternum 11 and yet another embodiment 801 having a plurality of closely spaced apertures 805, or slots positioned along the left and right sides of the plate body 807. Due to the variability of patient specific rib spacing such a design may be more practical by providing the operator more options to dock fasteners to the sternum plate.

Figure 16:
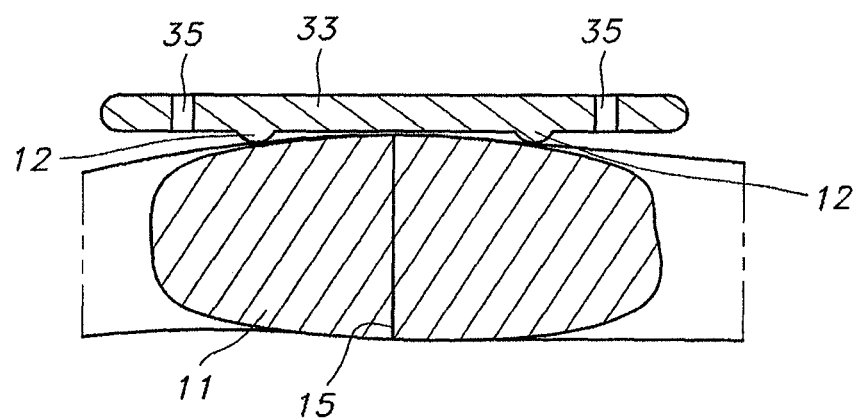
FIG. 16 is a section view taken along line 16-16 of FIG. 2.

FIG. 16 shows a cross section of the sternum and invention taken on line 1616 from FIG. 2. The torsion rails provide for a reduced surface contact area with the bone, allowing increased circulation of bodily fluids to the bone and other tissues. The torsion rails also provide additional stiffness to the plate.

Figure 17:
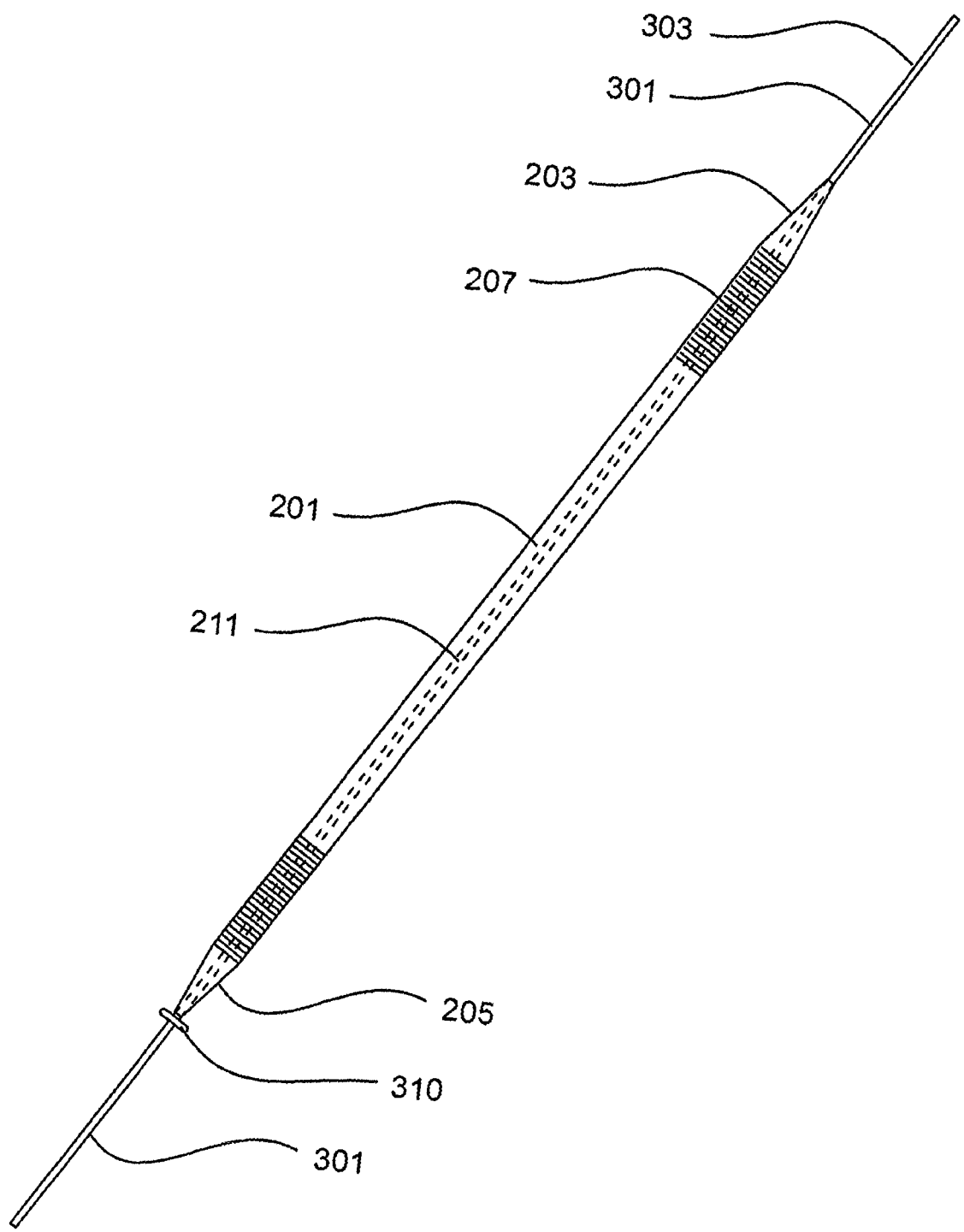
FIG. 17 shows an embodiment of the invention in which the locking fastener, in this case a double ended locking fastener, possesses a channel through which a guide wire may pass.
Figures 18, 19, 20:
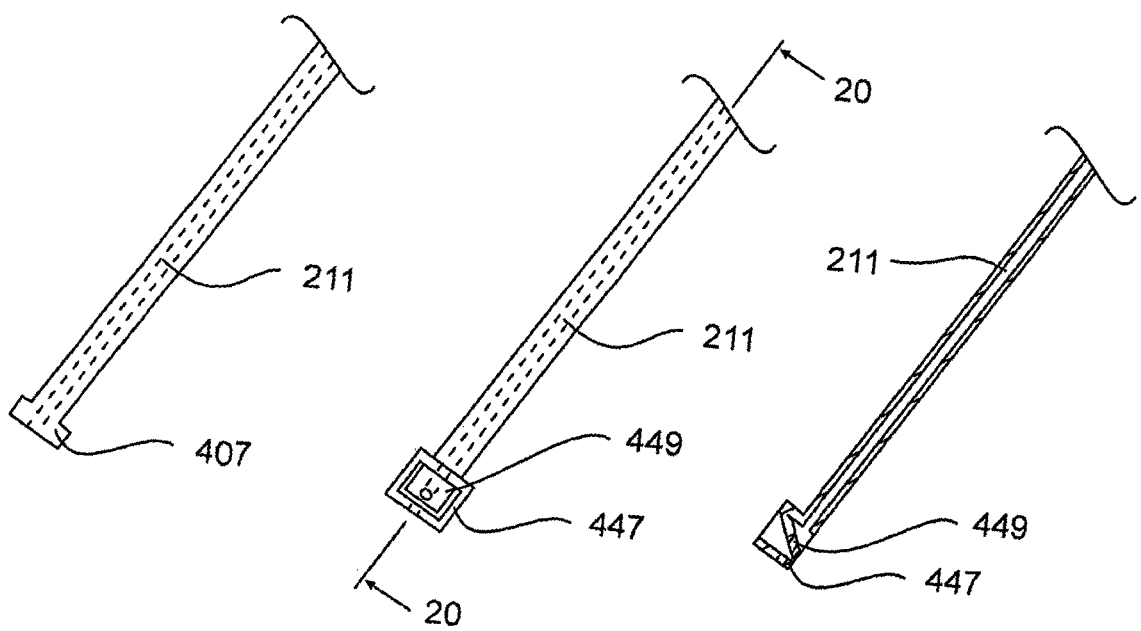
FIG. 18 shows a single headed embodiment of the locking fastener having a channel through which a guide wire may pass.
FIG. 19 shows a front view of a single ended embodiment of the locking fastener having a channel through which a guide wire may pass in which one end possesses a self locking mechanism to engage the locking fastener.
FIG. 20 shows a section view of a single ended embodiment of the locking fastener having a channel through which a guide wire may pass in which one end possesses a self locking mechanism to engage the fastener strap taken on line 20-20 of FIG. 19.

An alternative embodiment of the invention comprises of a flexible fastener, strap-like device, resembling a zip tie or cable tie. The fastener could be double ended, as shown in FIG. 17, where either end may be fitted into a ratcheting fastener or single ended, as shown in the partial view of the fastener in FIG. 18, 19, or 20. A single ended fastener such as FIG. 18, 19 or 20 would have a head at one end that may or may not have a slot with locking mechanism contained within that secures around the fastener profile resisting pullout when the textured and tapered opposite end of the fastener is inserted through the slot forming a closed loop. FIG. 18 shows a fastener without such a locking head, instead a widened head 407 provides a stop. FIG. 19 shows a fastener with such a locking head 447. FIG. 20 shows a section view of the fastener shown in FIG. 19 taken along line 20-20 showing a flexible cam or prong 449. A single ended fastener might also appear as previously described but without head or terminal endpoint 447 allowing it to join or be locked to another body containing a corresponding locking slot. A double ended fastener, as shown in FIG. 17, would be textured 207 and tapered at both ends 203, 205 allowing both ends to lock to another body or bodies when passed through corresponding locking slots or locking fasteners.

The cannulated core or canal 211 that extends from one end of a fastener body to the other along the long axis of the fastener is to allow the passage of a guide wire to aid in their insertion though soft, semi-dense, and potentially hard material such as various connective tissues, muscle, cartilage and bone. A guide wire, as shown in FIG. 17, with a "stop" 310 would allow the cannulated fastener to be advanced by pulling on the lead end 303 of the guide wire 301 allowing a cannulated fastener with a specially tapered tip at the lead end 203 to follow the guide wire tunneling through soft, semi-dense and potentially dense matter encountered along the pathway. A stop feature 310 incorporated into a guide wire 301 would prevent a guide wire from traveling freely past the trailing end 205 of the fastener 201 and entirely through the cannulated canal such as would happen with a guide wire without a stop. When passing a guide wire 301 with a stop through the cannulated canal of a fastener, the advancement of the guide wire through the canal is limited when the stop feature 310 incorporated into the guide wire meets the fastener end preventing the guide wire from freely passing through the cannulated canal and completely exiting the opposite end of the fastener. This is due to the stop 310 being larger in diameter than the cannulation aperture restricting the stop 310 and the trailing end of the guide wire behind it from entering the cannulated canal of the fastener. The stop 310 is placed along the guide wire in such a location as to allow a portion of the guide wire to extend beyond the tapered tip of the leading end of the fastener when fully inserted into the cannulated fastener at which point the stop is resting against the cannulated opening at the trailing end of the fastener. Thus, when a guide wire with stop 310 is fully inserted into a cannulated fastener, resistance results when pulling the exposed end of the guide wire at the leading end emerging from the cannulated canal at the leading end of the fastener. When the guide wire 301 is tensioned in this way and enough force is applied the fastener advances along with the guide wire. Once a cannulated fastener 201 has been advanced to a desirable resting position, the guide wire is no longer needed and is removed by grasping its exposed end at the trailing end of the fastener and pulling it completely from the cannulated canal 211 of the fastener and discarded. The specially tapered tip on the lead end of the fastener can be cut and removed thereafter. The tapered tip would preferably have a square pyramid tip, FIG. 22A, a triangular pyramid tip, FIG. 22B or a conical shaped tip, as shown in FIG. 22C. Such tip profiles could be equally suited for the fastener lead end and in the case of the double ended fastener, its trailing edge.

Such fasteners could be made of a thermoplastic polymer such as PEEK, nylon or resorbable polymer formulations. Potentially they could also be made of metallic materials including stainless steel, titanium, cobalt chrome and other alloys. They could be made of solid or braided material to enhance their malleability. Guide wires are typically made of stainless steel but could be made of other materials. Their diameter can range depending upon the dimensions of the fastener they are to be utilized with and strength requirements due to the density of the material they are intended to assist fasteners to tunnel through. The cannulated fastener may have a rounded profile as shown in FIG. 21A to avoid sharp edges, or may have quadrilateral profiles as shown in FIG. 21B.

Cannulated fasteners would be very useful in minimally invasive "keyhole" surgery where visibility and access are limited. Cannulated fasteners are a valuable component of circumfixation constructs described above. Cannulated fasteners may be used with other fixation devices such as plates, rods, nails and wires.

Cannulated fasteners might have barbed exterior surfaces, 273 or 283, allowing them to be inserted in one direction but resistant to pull out in the opposite direction.

The cannulated fasteners guide wire allows insertion of fasteners without the aid of a pilot hole. Under some conditions, a pilot hole may be useful to enter through extremely dense material. Guide wires are, as in the preferred embodiment, smooth, but in an alternative embodiment, a threaded tip may be present to guide in their insertion through dense material.

Figure 23:
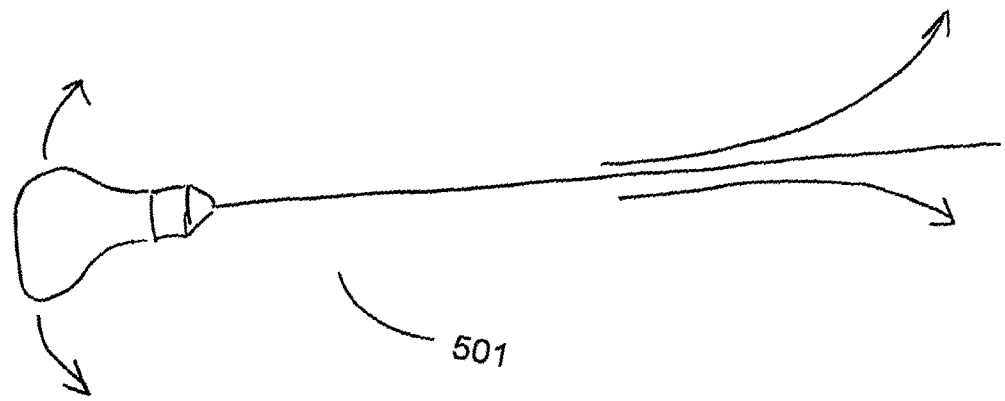
FIG. 23 shows a front view of an insertion tool with a mechanical insertion probe that allows the precise control and manipulation of a locking fastener for guidance upon human insertion of said fastener an embodiment of the invention.
Figure 24:
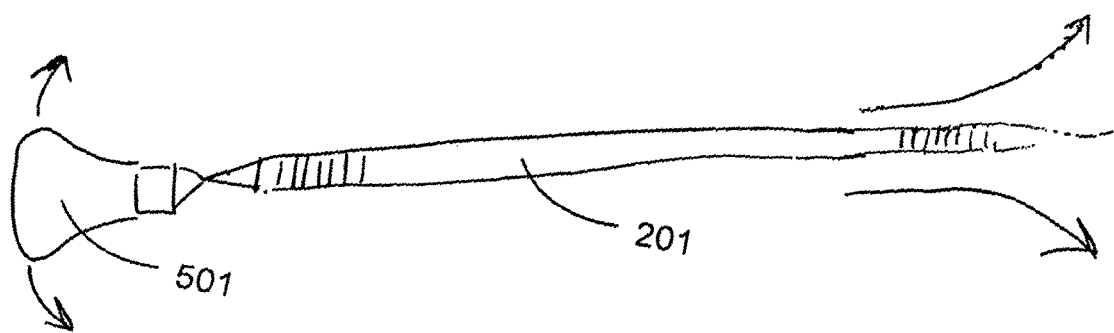
FIG. 24 shows a front view of an insertion tool with a mechanical insertion probe installed within a double ended locking fastener an embodiment of the invention.

Alternatively, a cannulated fastener might be aided in its placement by a mechanical instrument 501, such as shown in FIG. 23, that when the probed end of said instrument is inserted into the cannulated canal as shown in FIG. 24, of the fastener allows an operator to manipulate and guide a fastener to bend and move in a desirable direction. This is accomplished by the fastener being flexible and malleable, especially in one plane. For example, bending along the fastener's 201 wider cross section thickness provides less overall curvature, while bending along the fastener's thinner cross section thickness allows the tool and fastener to be bent in the desired direction. This capability may prove valuable in a variety of applications including minimally invasive or "keyhole" surgery where direct and indirect visualization is either limited or lacking completely. Such an instrument might also incorporate an imaging capability such as fiber optics giving the operator the capability of indirect visualization of the pathway the device and fastener are traveling.

The above embodiments possess single ended and double ended locking fasteners which are connected to circumfixation plates through specially designed slots incorporated into the plate body. Each slot within the plate body designed to self lock contains a locking mechanism that secures around the fastener profile when inserted and advanced through a slot from one direction and resistant against pullout when force is applied in the opposite direction.

Figure 25:
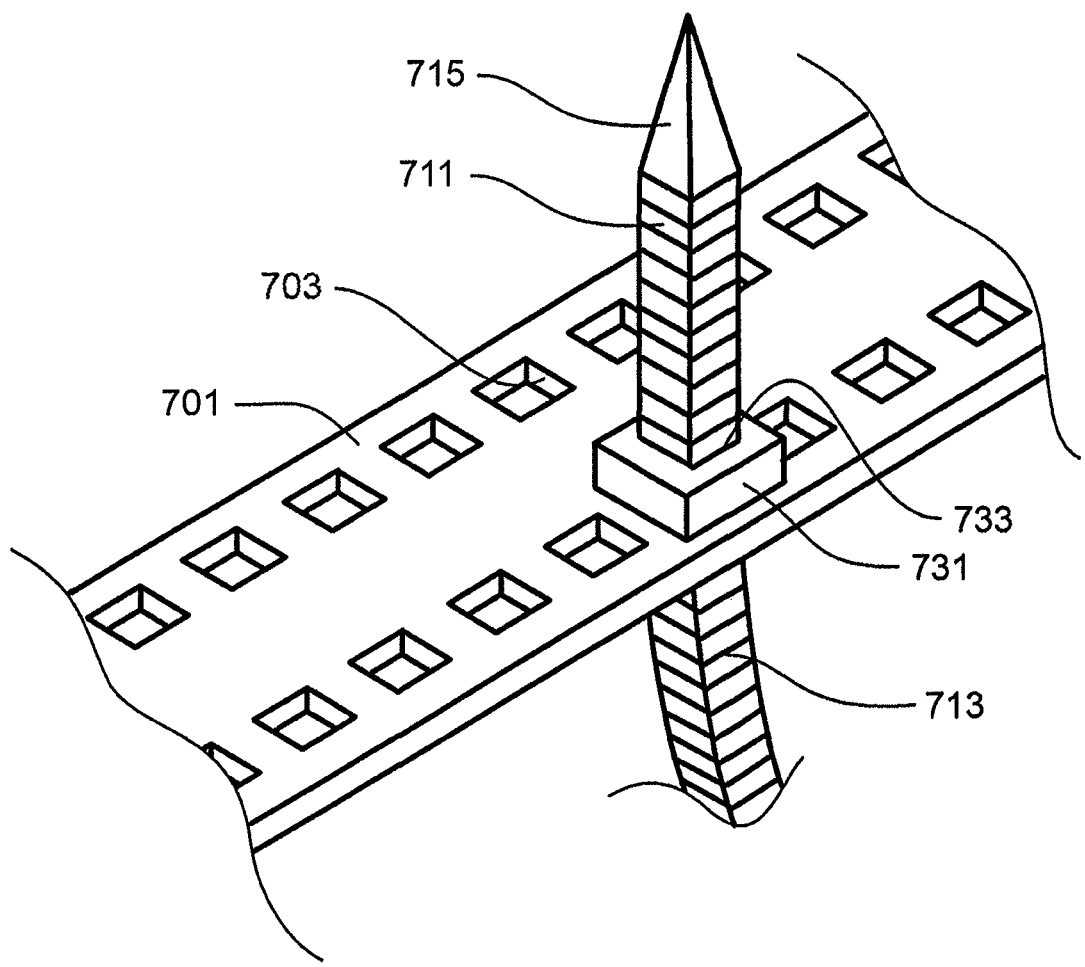
FIG. 25 shows an embodiment of the invention having a plate with non locking apertures and a separate locking nut engaging a fastener strap.

An additional embodiment of the invention is shown in FIG. 25 securing locking fasteners whereby the locking mechanism is not contained within the plate body or incorporated within the specially designed slots, or apertures 703, formed in the plate that accept the fastener profile when the fastener 711 inserted. This method involves the use of a locking nut 731 with a slotted center core 733 containing a locking mechanism within that when passed over the profile of a locking fastener 711 locks around the profile, preferably engaging textured ribs 713 molded into the sides of the fastener 711. Fasteners 711 can be advanced passively through locking nuts 731 in one direction but are resistant pullout after insertion when force is applied from the opposite direction. Such locking nuts 731 could be used with locking fasteners 711 and circumfixation plates 701 whereby the slots 703 contained in the plates 701 do not possess locking mechanisms integrated into the plate body 701 and locking fasteners 711 can travel forward and backward through the slots 703. Locking nuts 731 would be placed over the locking fastener 711 ends 715 after they are inserted through the passive slots 703 contained in a circumfixation plate 701.

Figure 26:
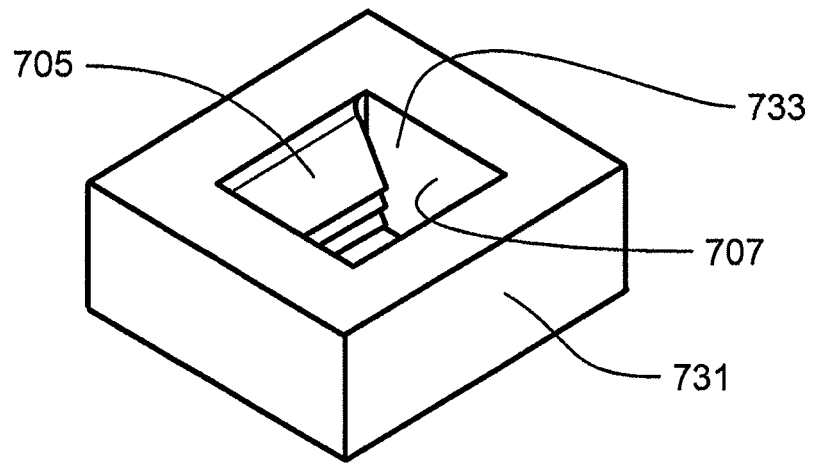
FIG. 26 shows a perspective view of the locking nut.

FIG. 26 is a perspective view of an example of a locking fastener 731. In this embodiment, locking tabs 705 are positioned on opposing sides of the nut 731 aperture 707. While two locking tabs 705 are used in this embodiment, a single locking tab, or a plurality of tabs may be placed around the nut 731 aperture 707.

Figure 27:
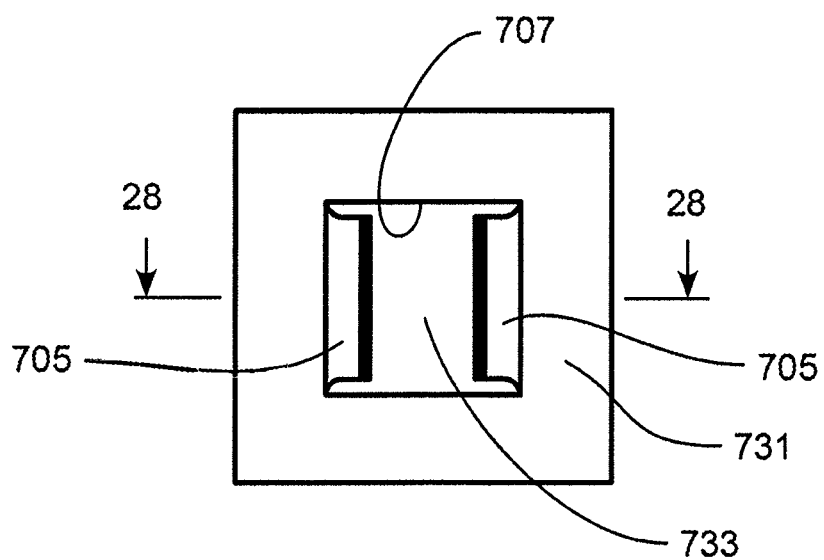
FIG. 27 shows a top view of a locking nut.

FIG. 27 shows a top view of the locking nut 731. The locking tabs 705 can be seen on opposing sides of the aperture 707.

Figure 28:
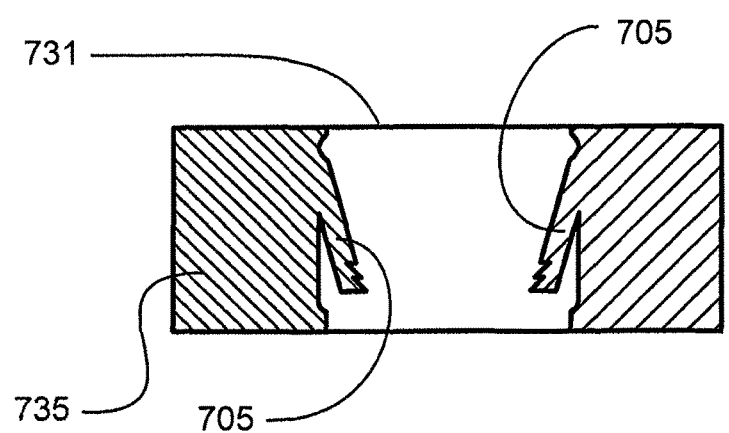
FIG. 28 shows a section view of a locking nut taken on line 28-28 of FIG. 27.

FIG. 28 is a cross section taken on line 28-28 of the locking fastener 731 shown in FIG. 27. The locking tabs 705 are shown as protruding from the locking nut 731 body 735. These locking tabs 705 engage textured ribs 713 of the fastener 711.

Figure 29:
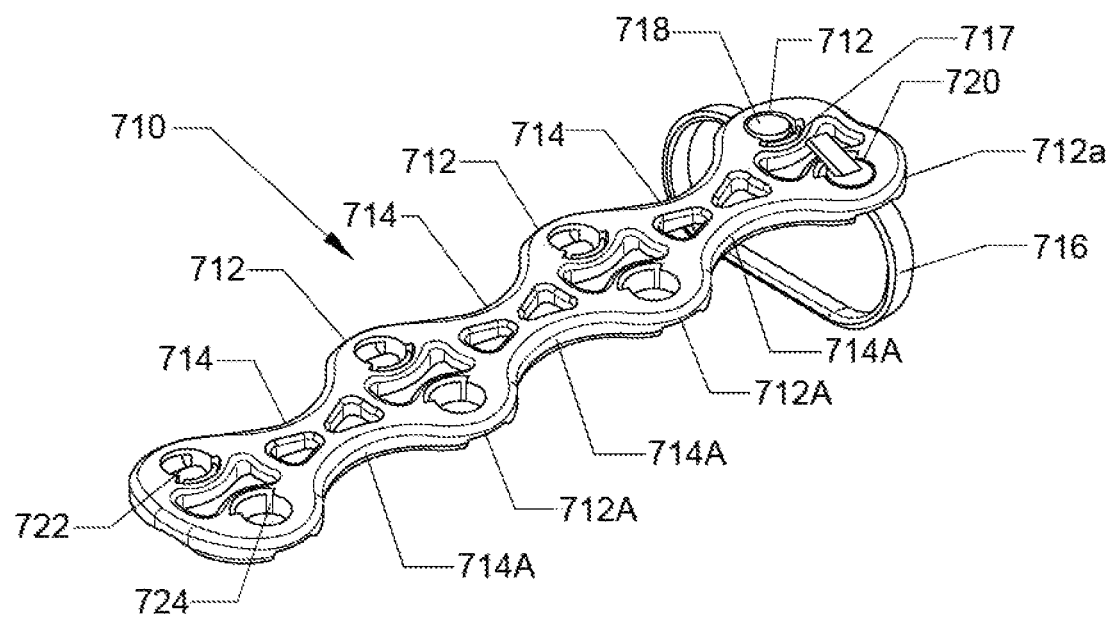
FIG. 29 is a perspective view of a multi-protrusion embodiment of the invention.
Figure 30:
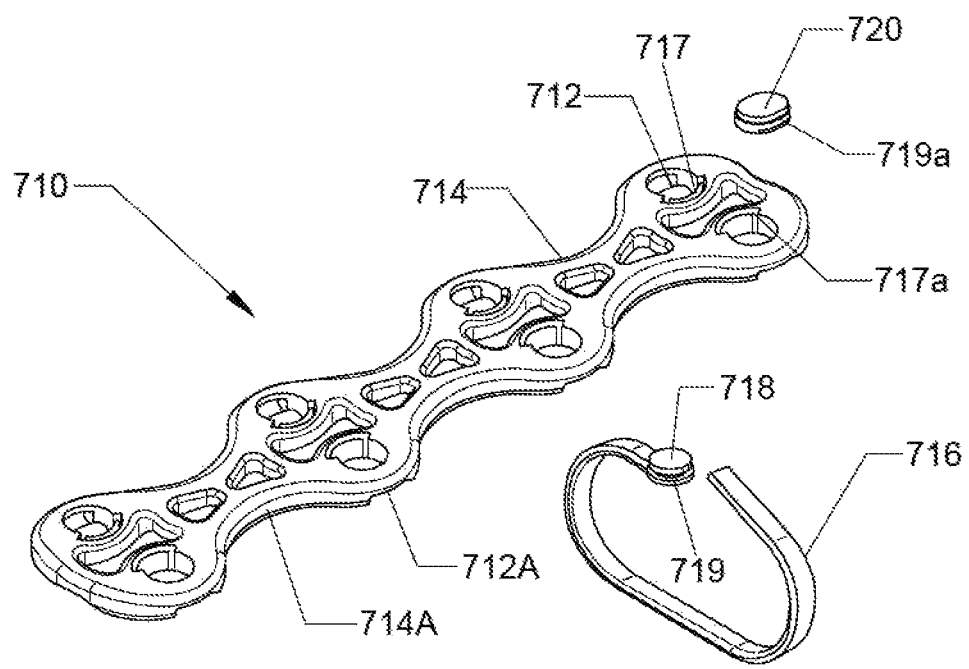
FIG. 30 is an exploded view of the embodiment of FIG. 29.

FIGS. 29 and 30 depict another potentially preferred embodiment of the invention, in this alternative a multi-fastener circumfixation device 710 including a sternal body plate assembly consisting of a plate having expanded portions 712, 712A, and narrowed portions 714, 714A, a cable tie-like fastener 716 and a locking insert 720. The fastener 716 and locking insert 720 will be further described below. The plate is designed to lie on the relatively flat anterior surface of the sternal halves and to be "splinted" to the bone by the fastener 716 which is inserted through the soft tissue between the ribs on the first side in an anterior-to-posterior direction, wraps underneath both sternal halves, is then inserted through the soft tissue between ribs on the second side in a posterior-to-anterior direction and finally inserted through the locking insert 720 and tightened. The fastener 716 is held in place by a rotating button 718 present within one expanded portion 712 of the plate opposite of the locking insert 720 present within the opposing expanded portion 712A. FIGS. 29 and 30 show the fastener after it has been tensioned and the excess length cut off. The significant features of the plate are:

The expanded portions 712, 712A of the plate 710 correspond to the intercostal spaces in the sternal body. The width of the plate across these wings is still significantly less than the width of the sternum. This allows/forces the fastener 716 to exit the plate and reenter the locking insert 720 at an oblique angle that is closer to being parallel with the anterior surface of the sternum. As the fastener 716 is tensioned through the locking insert 720, the force vectors provide a greater force in the medial-lateral direction and a lesser force in the anterior-posterior direction. The result is more of the tensioning force squeezing the sternal halves together. Contrast this with FIGS. 16 and 25, above, where the force vectors resulting from tensioning the fasteners serve to primarily compress (splint) the plate to the sternal halves without adequately addressing the need to compress the sternal halves to promote stability and healing.

Such a plate 710 is thus designed to be more flexible along the midline allowing the wings to flex and conform to the anterior surface of the sternum as the fastener(s) 716 is tensioned. The expanded portions 712, 712A in the plate 710 can thus be sized and located to optimize flexibility and provide visualization of the sternotomy gap.

Cavities in the expanded portions 712, 712A allow for placement of the button end 718 of the fastener 716 and the locking insert 720. Tabs 717, 717a on the plate 710 mate with grooves 719, 719a on the button 718 and the locking insert 720 to insure correct orientation and to provide retention.

The button 718 (and the fastener/strap 716) and the locking insert 720 can rotate within the cavities of the plate 710 to allow the fastener/strap 716 to adjust to the sternal anatomy. It is not always feasible to have every wing (expanded portion 712, 712A) on the plate 710 fall precisely between the ribs or where the sternum is most narrow and this rotation allows the plate assembly to adjust to the particular patient anatomy while still providing for optimal tensioning of the fastener 716. Additionally this rotational adjustability should reduce the number of discreet plate sizes/configurations required for the patient population.

Figure 31:
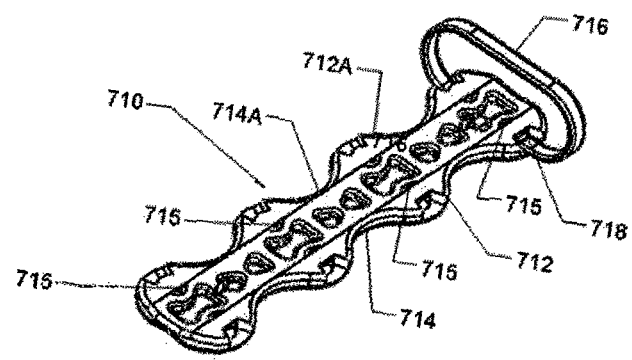
FIG. 31 is a rear view of the embodiment of FIG. 29.

The underside of the plate, as shown in FIG. 31, for instance, also contains some notable features: small projections 715 along the midline of the plate can be included to maintain plate position during implantation. Shown on this illustration are a series of thin "keels" 715 intended to engage the sternotomy gap to maintain the midline positioning of the plate as the fasteners 716 are being tensioned. The size, shape and number of these keels 715 could be optimized to maintain plate position without adversely affecting the implant's ability to compress the sternotomy gap. In another embodiment, these keels 715 could be replaced by small spikes or a textured underside to provide the required stability. In this embodiment the central underside of the plate 710 is relieved. This promotes flexibility of the wings 712, 712A as noted above and minimizes direct contact of the plate and the healing site along the sternotomy line. The underside view of the plate 710 shows the oblique entry and exit paths of the fastener/strap 716 as well as the angulation provided by the rotatable button and lock.

Figure 32:
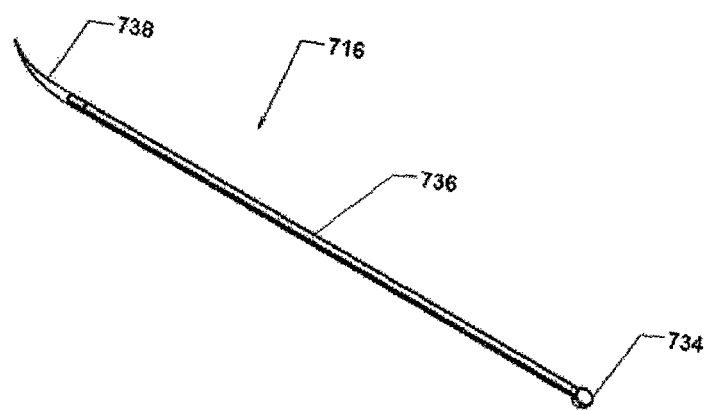
FIG. 32 shows a perspective view of a fastener of the invention.

FIG. 32 illustrates the fastener/strap 716 prior to installation in the plate. At the top end is an integral needle like tip 738 for piercing the soft tissue in the intercostal spaces. At the opposite end is the button 734 which retains the fastener in the plate and allows for subsequent rotation. In between is the body of the strap 736. In the embodiment where the fastener is a solid cable tie-like strap the body connects the needle end to the button. In another potentially preferred embodiment where the fastener is a braided/woven design, the braid/weave extends from the button to a short, solid transition area proximal to the needle end. This allows the surgeon to cut the needle off once it has been used to pierce the soft tissue and still have a solid end for ease of insertion through the plate and locking insert. There are a multitude of braided or woven configurations known to those skilled in the art.

Braided materials can be constructed of many different materials, from metals to polymers and designed to produce optimal balances of flexibility and tensile strength. Such materials require the need for a solid transition element in a braided construct, as the cut ends fray unacceptably if cut and not fused. The significant features of a braided fastener include improved handling for the surgeon. The braided fastener would be more flexible and resemble a heavy suture more than a semi-rigid strap. The greater flexibility of the braid would allow it to better conform to the irregular surfaces of the sternum as it is wrapped around and tensioned. The resulting greater contact area would decrease the local areas of stress in a bone plagued by poor cortical density and thickness. Greater flexibility will result in fewer and smaller gaps between the fastener and bone as it negotiates tight bends and curves. This results in more predictable tensioning and less unwanted movement post-operatively.

A braided fastener has an intrinsic surface texture for engagement with a locking mechanism employing teeth to grip the fastener and prevent reverse motion. Such a braided fastener further offers greater patient safety upon removal. Unlike conventional wire or the Synthes ZipFix, the cut end of a mesh fastener would produce a soft, frayed end on a flexible strand. Contrast that with a sharp cut end on a semi-rigid wire or ZipFix and consider them being pulled blindly around the back side of the sternum for removal. A braided fastener may also prove to be so beneficial that some surgeons may wish to use a locking braided cable tie alone, in place of wires, ZipFix, the "circumfixation plate" or even as the means of securing the manubrium when used in conjunction with the "circumfixation plate". Such a device would itself be novel and valuable. Combining the fastener button with the insertion lock produces just such a device as shown below in FIG. 8.

Figure 33:
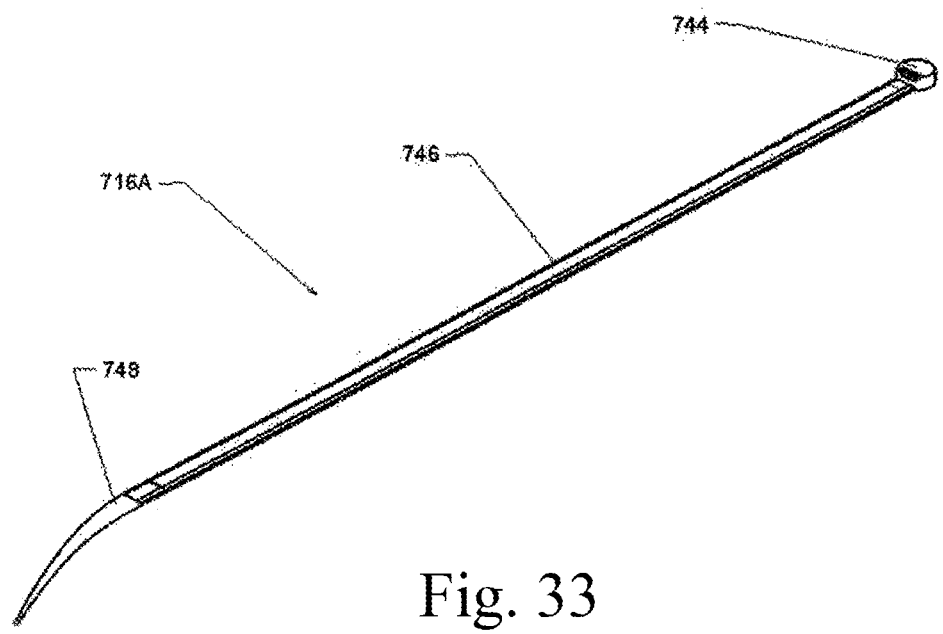
FIG. 33 shows perspective view of a fastener of the invention with a stationary retention device attached thereto.

FIG. 33 provides a different type of a potentially preferred fastener 716A for utilization with the plate 710. This alternative fastener 716A includes a piercing needle tip 748 and a body portion 746, but the other end is a locking mechanism 744.

Figure 34:
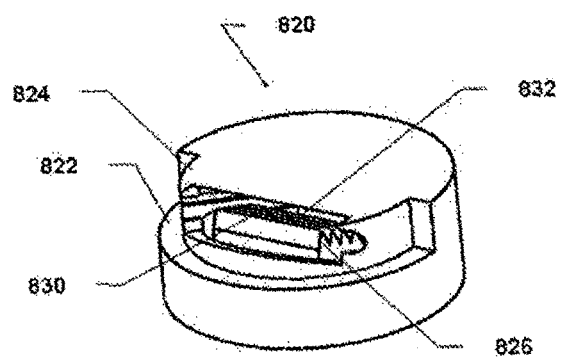
FIG. 34 is a perspective view of an inventive revolving locking mechanism.
Figure 34A:
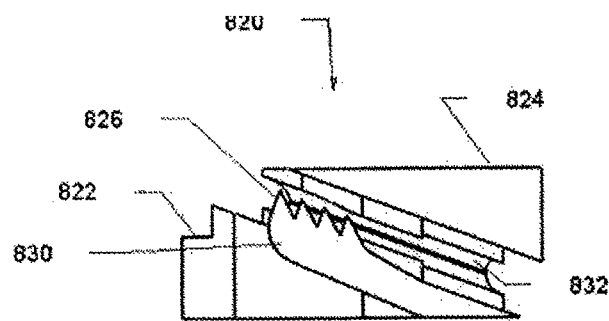
FIG. 34A shows a cross-sectional view of the mechanism of FIG. 34.
Figure 35:
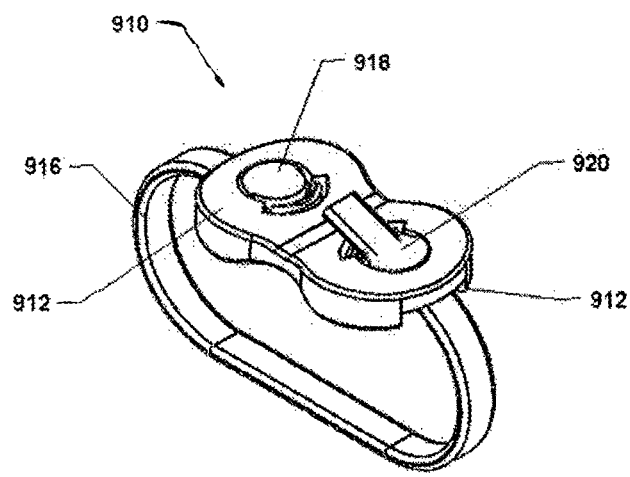
FIG. 35 is a perspective view of a single-protrusion bone splint of the invention.
Figure 35A:
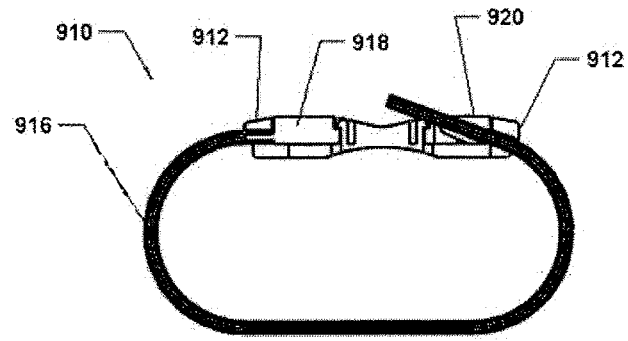
FIG. 35A is a perspective cross-sectional view of the embodiment of FIG. 35.

FIG. 34 shows a profile view of a potentially preferred locking mechanism 820 for utilization within a plate. Such a mechanism 820 includes a shoulder 822 for retention within a plate, a top surface 824, and a one-way locking tab 826 with teeth 830 to grab a fastener end when inserted through an oblique slot 832 adjacent thereto. In cross-section, FIG. 34A shows the same locking mechanism 820 providing a view of the oblique slot 832. FIGS. 35 and 35A thus show the overall single plate structure 910 with the locking mechanism 920 and retention button 918 present within the coverage plate portion 912 with the strap 916 locked therein (and thus to a degree that would permit retention around a subject sternum and a single set of interstitial spaces. The fastener 916 may be cut to the level of the plate surface 912 if desired.

Figure 36:
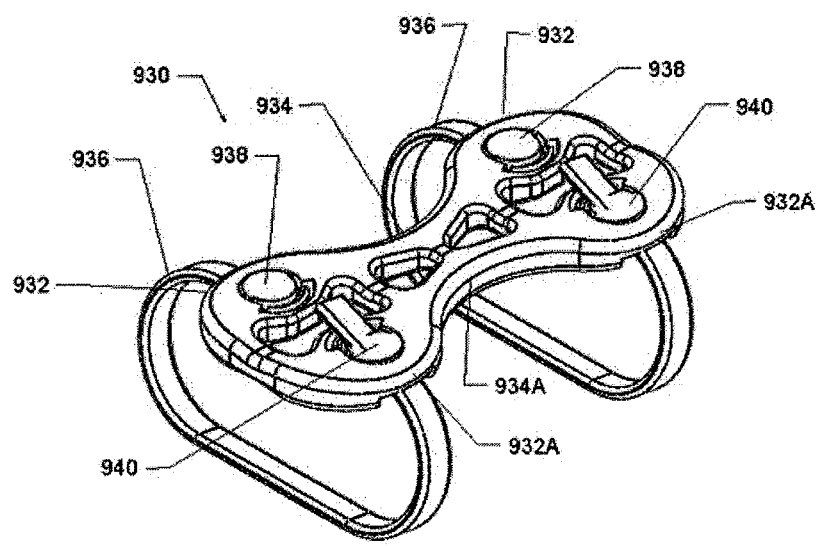
FIG. 36 is a perspective view of a double-protrusion bone splint of the invention.

A double wing plate 930 is provided in FIG. 36, including said two wings 932, 932A and a single narrowed portion 934, 934A with two fasteners 936 and two sets of buttons 938 and locking mechanisms 940, as above. This would allow for coverage of a greater area of a subject sternum with secured fastener attachment through and around two interstitial space sets.

FIGS. 36 and 36A thus depict a revolving lock (locking insert) 940. In FIG. 36 you can clearly see the groove (cutout) which mates with the snap-fit tab on the plate to provide retention, alignment and limits rotation as desired. The section view illustrates the spring loaded, uni-directional locking mechanism, similar to that found on an industrial cable tie. The utilization, then, of even larger winged plates may be employed, if desired, or a series of single or double winged structures may be utilized to effectuate the necessary sternum fixation in this manner.

Figure 37:
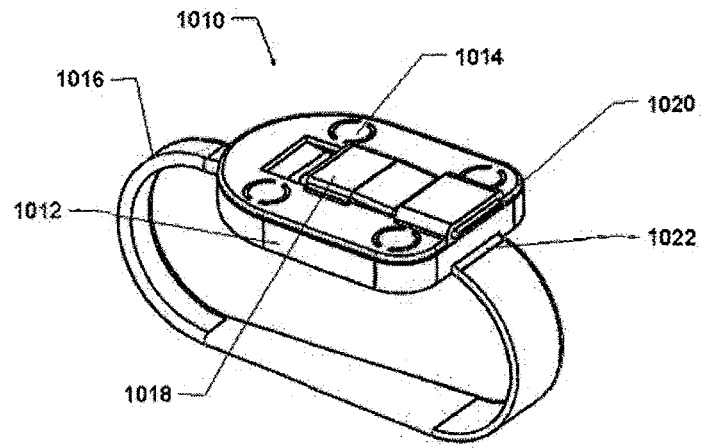
FIG. 37 is a perspective view of a bone splint including a secondary locking mechanism.
Figure 37A:
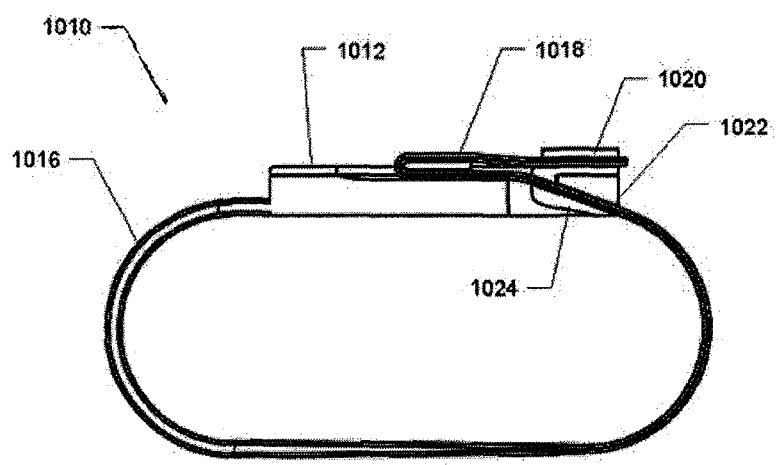
FIG. 37A is a side cross-sectional view of the embodiment of FIG. 37.
Figure 38:
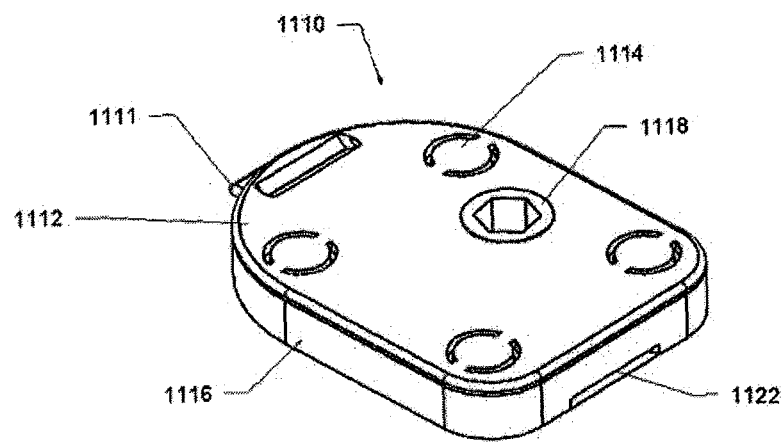
FIG. 38 shows a perspective view of a cam-type locking mechanism for utilization with an inv.

FIGS. 37 and 38 illustrate (one from the top, the other from the bottom) another configurations that may also be potentially preferred for attachment of a splint to a subject sternum. The exact size and shape of the plates is less important than the concept of multiple configurations—not just multiple sizes. FIG. 37 shows, again, a single wing configuration 1010 with a base 1014, a fastener receiving slot 1020, a one-way rotating cam with a drive socket 1018 (here a hexagonal type as in FIG. 38, for instance). The plate 1010 includes a top portion 1112 that may snap into place to secure the fastener 1016 that is introduced through securing slot 1120 and a separate, opposite securing slot 1122. Importantly, as noted above, multiple numbers of such snap-on securing plate structures 1110 may be utilized along the subject sternum for fixation purposes. In such situations, then, a one or two fastener "mini-plate" for the manubrium might be an ideal complement to a sternal body plate. Since the manubrium is often the best bone in the sternum and the first line of defense against the medial-lateral separation of the sternotomy post fixation, such fixation in that area is potentially the best for this purpose.

Figure 38A:
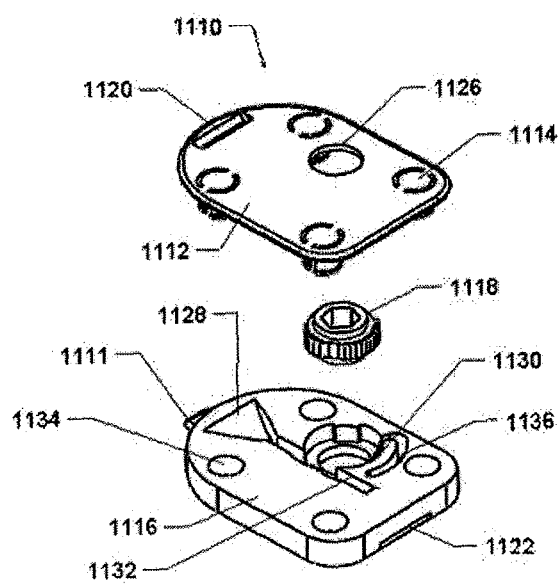
FIG. 38A is an exploded view of the embodiment of FIG. 38.
Figure 39:
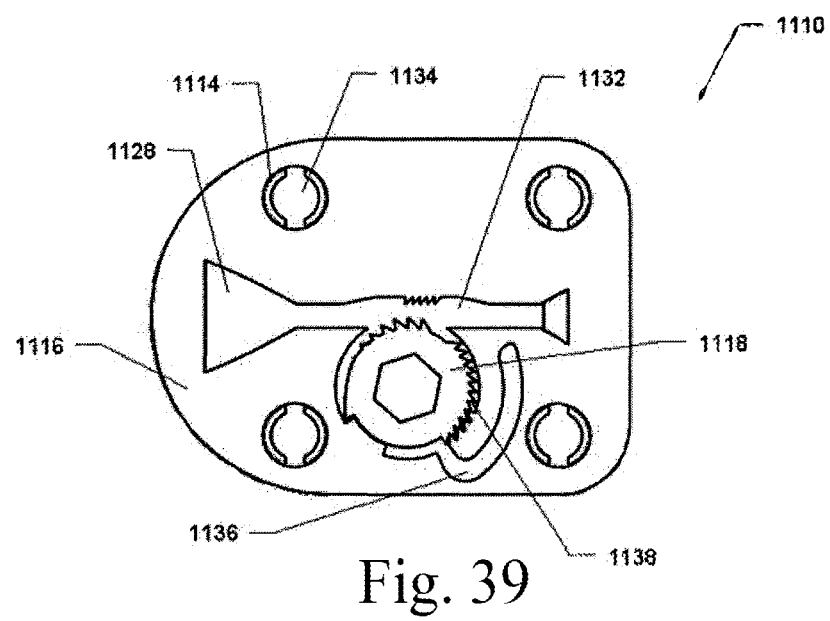
FIG. 39 is an top view of the bottom portion of the embodiment of FIG. 39.
Figure 40:
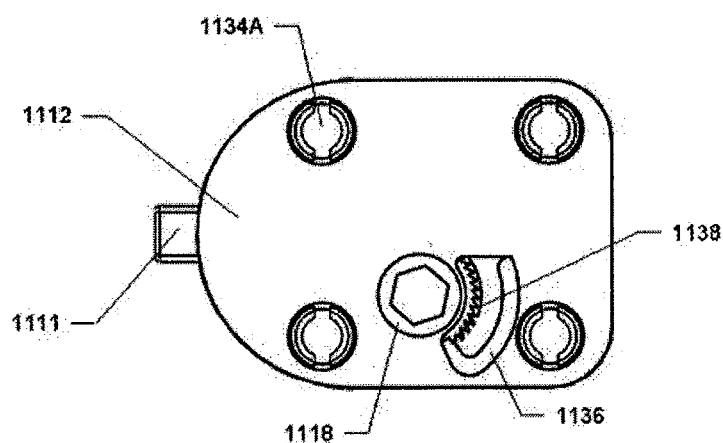
FIG. 40 is a bottom view of the bottom portion of the embodiment of FIG. 38.
Figure 41:
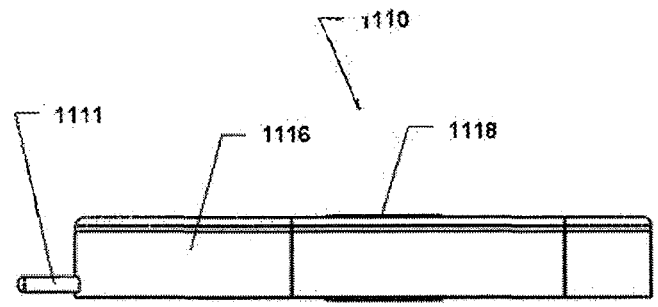
FIG. 41 is a side view of the bottom portion of the embodiment of FIG. 38.

FIG. 38A shows the cam-type snap-on plate structure 1110 with the top cover 1112 with snap bosses 1114, and including an access hole 1126 for hexagonal tool (not illustration) insertion and an upper slot 1120. The cam 1118 is provided to allow access to the complementary hexagonal portion (for the tool insertion) (1156 of FIG. 42, for instance) that is placed within a tooth-springed tab 1130 to allow for one-way rotation via a cavity 1136 that allows spring tab deflection during cam rotation (situated within the lower portion 1116). The lower portion 1116 also includes recesses 1134 for snap introduction, and an exit slot 1128 for the fastener 1111. FIG. 39 shows the underside of the entire plate 1110 with the snap bosses 1114 in place within the recesses 1134 and the cam 1118 in place within the tooth-spring tab 1138 and the deflection cavity 1136. The exit slot 1128 leads to the base slot 1132 for the fastener 1111, as well. FIG. 40 provides a view of the top of the entire plate 1110 with the top cover 1112, the hexagonal recess 1118 and the cam 1138 (teeth at least). FIG. 41 thus shows a side view of the plate 1110 with a raised hexagonal recess 1118, the fastener 1111 introduced therein and the side wall 1116 protecting the internal portions.

FIGS. 39 and 39A thus depict a fixed angle (no rotation) design with an auxiliary locking mechanism. In addition to the locking mechanism found in the revolving lock (FIGS. 36 and 36A), the flexible fastener is fed back over a sharp or toothed prominence and captured from above with a tab that folds down and locks in place (particularly to capture a cut end of a fastener with great reliability).

FIGS. 40 and 40A thus illustrate an additional locking mechanism for a fastener which utilizes a one-direction rotating cam to clamp down on the braid (or like structure). In practice, the fastener 1111 is fed through the front slot 1122 at the bottom and exits through the top slot 1128. The cam 1118 is in the neutral (or zero interference position). When the fastener 1111 is properly tensioned, the cam 1118 is rotated (in a clockwise manner) to crimp the fastener 1111 (again, such as a braid structure) between the teeth 1138 on the wall of the base plate 1116 and the vertical splines on the cam 1118. A spring loaded pawl 1136 molded into the base plate 1116 prevents reverse rotation of the cam 1118.

Figure 42:
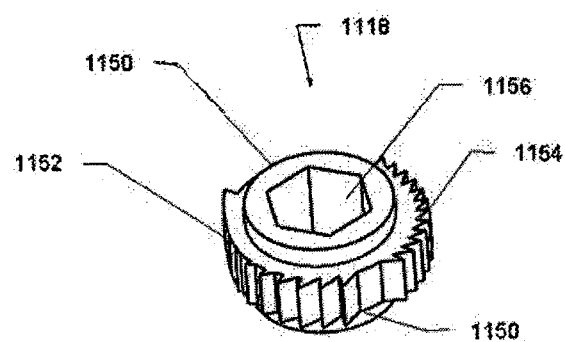
FIG. 42 is a perspective view of the cam gear of the embodiment of FIG. 38.
Figure 43:
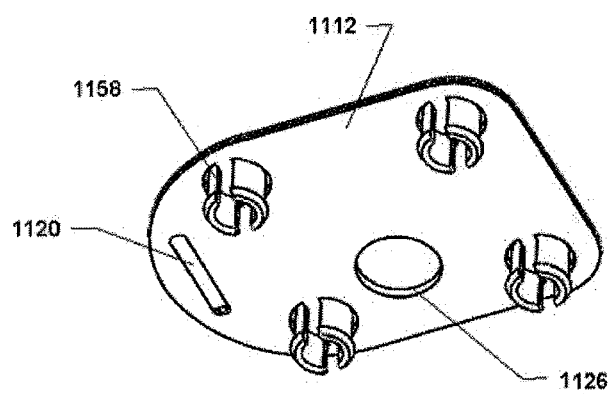
FIG. 43 is a bottom perspective view of the top plate of the embodiment of FIG. 38.
Figure 44:
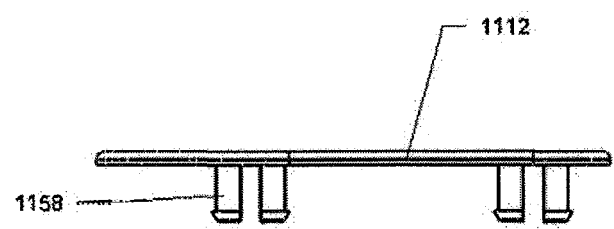
FIG. 44 is a side view of the top plate of the embodiment of FIG. 38.
Figure 45:
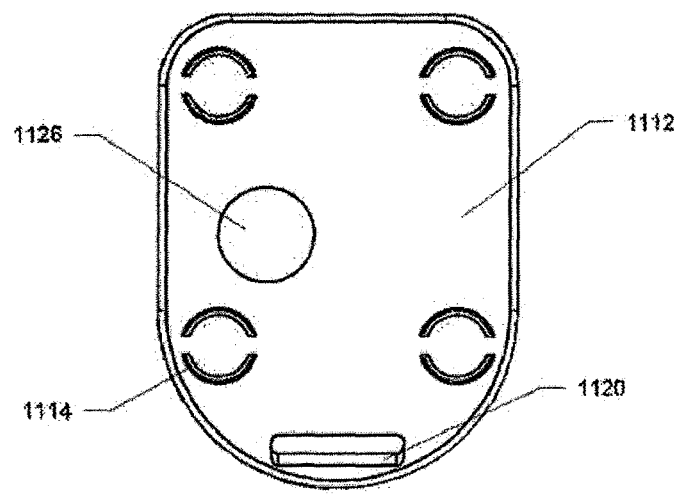
FIG. 45 is a top view of the top plate of the embodiment of FIG. 38.

FIG. 42 shows the cam 1118 in greater detail. An internal hex drive socket 1156 extends from a hub 1150 (upper and lower) with fastening engaging external teeth 1152 and one-way motion external teeth 1154. FIG. 43 provides a more succinct view of the underside (internal) top cover 1112 with snap bosses 1158 (with barbed distal ends) to snap within the recesses of the lower portion. An opening 1126 for insertion and extension of the cam (1118 of FIG. 42) is provided, as well as an exit slot 1120 for the fastener (1111 of FIG. 40). FIG. 44 shows the same top cover in side view. FIG. 45 provides the top view of the top cover 1112 with the snap boss external portions 1114 to allow for proper alignment of the two portions.

Figure 46:
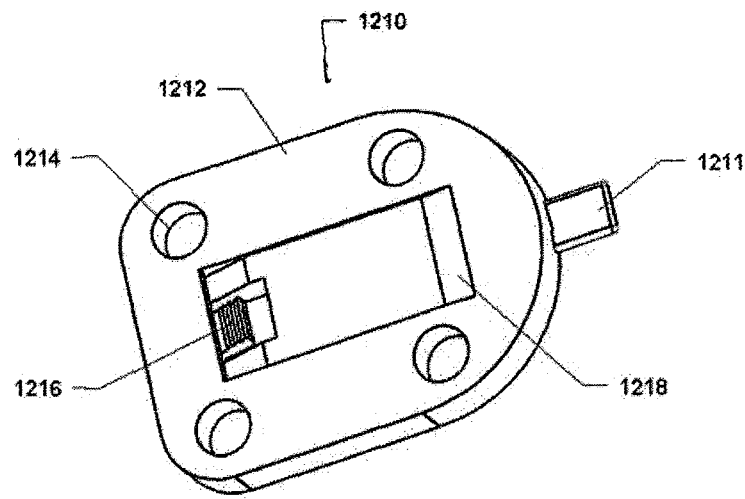
FIG. 46 is a perspective top view of a fixed angle auxiliary locking mechanism for utilization with an inventive bone splint.
Figure 47:
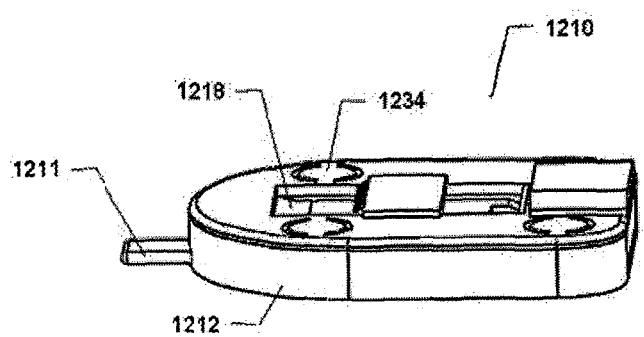
FIG. 47 shows a side view of the embodiment of FIG. 46.

Another alternative, potentially preferred embodiment of this single wing structure is provided in FIGS. 46-47. Such a structure 1210 allows for a fixed angle, single fastener device 1211 introduction with a secondary locking mechanism 1216. The mechanism is present on the top cover base 1212 with an exit slot 1218 (and multiple recesses for snaps 1214). The locking mechanism 1216 thus engages the fastener 1211 upon introduction therein through angled teeth. FIG. 47 shows the same structure 1210 in side view.

For this invention, then, the term "locking mechanism" may be of any type as described above or that provides effective and reliable retention of one end of a fastener. With the cam device, described above, the single direction rotation corresponds to tightening of the fastener without any possible relaxation, thereby locking and tightening simultaneously. Additionally, such described locking mechanisms (rotating, fixed, secondary, and cam) may be properly utilized in conjunction with a double-ended fastener for even greater reliability. As alluded to above, as well, all such components and devices can be produced with any proper materials for resiliency, flexibility, etc., as needed, and that is acceptable for such "implant"-type structures within the human body. The fasteners and the plates may be manufactured of, clearly, different types of materials for such end uses, basically any that allow for such purposes and, again, that are or may be considered accepted and/or approved for implantation and internal splint utilization. As merely examples, then, such a fastener may be manufactured from braided stainless steel fibers and the plate from a polymer such as PEEK or PEKK, again, as non-limiting examples. Furthermore, the multi-winged plates of, for example, FIG. 37 may be modified to incorporate a "hinge point" at the sternal angle to provide a full-length, properly contoured sternal plate.

Thus, with these different types of structures, all fall within the basic consideration of fastened sternal plate devices to permit not only proper healing subsequent to a sternotomy, but also the ability to provide flexibility for ribcage movements (such as breathing and diaphragm requirements) as well as a protective cover for sensitive sternal areas. The different mechanisms described above all provide these benefits, in an area heretofore unexplored within this industry.

Overall, then, as described herein, the technique referred to as circumfixation could have applications in rib fracture fixation, clavicle fracture fixation, scapula fracture fixation, proximal and distal femur fixation, proximal and distal tibia fixation, fibula fixation, proximal and distal humerus fixation, proximal and distal radius and ulna fixation, wrist bracing and/or reconstruction, ankle bracing and/or reconstruction, spinal bracing and/or reconstruction, pediatric fracture fixation, periprosthetic fracture management and fixation, veterinary fracture fixation and possibly other unidentified applications. Circumfixation could also prove to be a valuable method of temporarily stabilization of open fractures and comminuted open fractures such as those occurring on the battlefield. The general invention thus comprises, in terms of post sternotomy (and the like) surgical procedures, a plate contoured to lie passively against the forward facing aspect of the human sternum when placed directly on the irregular surface of the target sternum, and zip tie-like fasteners to secure the plate around the target sternum, thus securing the plate to the target sternum. Thus, the herein described invention allows for a reduction post-operative pain for the target patient as well as early post-operative mobilization thereof. Such beneficial activities may thus lead to earlier rehabilitation and discharge, and also accord a reduced potential for infection (as well as a reduced propensity to contract hospital-acquired pathogens). The device is intended to be biocompatible allowing it to remain in the body permanently, too. The device is intended to be inert and radiolucent causing no interference with any testing, diagnostic or imaging technology applied to the patient postoperatively.

The free areas of the plate structures described herein may also be utilized to house different devices for various results, including therapeutic activities (such as drug dosing), diagnostic activities (such as heart monitoring), and the like, without limitation, that might benefit from such in vivo delivery and that would not interfere with the healing process. For instance, the delivery of suitable materials to aid in the healing of the sternum in addition to the splint benefits provided could be accomplished in this manner.

Furthermore, while the term "circumfixation" in relation to this invention is described as a manner for securing and fixating cut or fractured bones avoiding the use of bone penetrating anchors such as screws, pins, blades, etc. to achieve stabilization, it should be noted that future designs of circumfixation devices could include the addition of such bone anchors which could enhance and expand the range of clinical applications of such an activity.

It should be understood that various modifications within the scope of this invention can be made by one of ordinary skill in the art without departing from the spirit thereof. It is therefore wished that this invention be defined by the scope of the appended claims as broadly as the prior art will permit, and in view of the specification if need be.

What is claimed is:

1. A bone plate assembly, comprising:
   a plate having a plurality of apertures formed through the full thickness of the plate, with at least two of the plurality of apertures being positioned proximal to lateral edges on opposing sides of the plate;
   one or more fasteners each having a first leading end, and a second end opposite the first leading end, each fastener being configured for the first leading end to pass substantially around a portion of bone and through at least one of the apertures for locking engagement to establish compression with adjustable tension between the plate and the bone;

a plurality of fastener attachments, each being incorporated with one of the apertures and configured to allow the first leading end of one of the fasteners to freely pass through one of the apertures in a first direction, and to resist fastener movement in a second direction opposite the first direction;

each fastener attachment comprising a locking nut having a base slot that accommodates entry of one of the fasteners first leading end into the fastener attachment to accept and secure the fastener attachment;

and wherein each fastener comprises ribs configured to engage an interior surface of one of the fastener attachments, thereby resisting movement of each fastener in the second direction opposite the first direction.

2. The bone plate assembly of claim 1, wherein the one or more fasteners comprises at least two fasteners, each of which engages one of the fastener attachments incorporated with one of the apertures of the plate to provide tensioning at the first leading end, the second end, or both ends thereof for simultaneous tensioning and locking of each fastener through the respective fastener attachments on opposing sides of the plate.

3. The bone plate assembly of claim 1, wherein at least one of the fasteners further comprises a cannulation aperture and a cannulated core for receiving a guide wire that assists movement of the respective fastener in the first direction, the guide wire comprising a stop configured to prevent movement of the guide wire in a direction opposite the first direction, and wherein the cannulation aperture has a smaller radius than a radius of the stop.

4. A bone plate assembly, comprising:

a plate having a plurality of apertures formed through the full thickness of the plate, with at least two of the plurality of apertures being positioned proximal to lateral edges on opposing sides of the plate;

one or more fasteners each having a first leading end, and a second end opposite the first leading end, each fastener being configured for the first leading end to pass substantially around a portion of bone and through at least one of the apertures for locking engagement to establish compression with adjustable tension between the plate and the bone;

a plurality of fastener attachments, each being incorporated with one of the apertures and configured to allow the first leading end of one of the one or more fasteners to freely pass through one of the apertures in a first direction, and to resist fastener movement in a second direction opposite the first direction;

each fastener attachment comprising a base slot that accommodates entry of one of the fasteners first leading end into one of the plurality of fastener attachments to accept and secure the fastener, and an exit slot through which the fastener first leading end exits the fastener attachment; and at least one of the one or more fasteners comprising a head located proximal to the first leading end, wherein the head is configured to be secured by one of the plurality of fastener attachments, thereby restricting movement of the fastener in the second direction opposite the first direction.

5. The bone plate assembly of claim 4, wherein the one or more fasteners comprises at least two fasteners, each of which engages one of the fastener attachments incorporated with one of the apertures of the plate to provide tensioning at the first leading end, the second end, or both ends thereof for simultaneous tensioning and locking of each fastener through the respective fastener attachments on opposing sides of the plate.

6. The bone plate assembly of claim 4, wherein at least one of the fasteners further comprises a cannulation aperture and a cannulated core for receiving a guide wire that assists movement of the respective fastener in the first direction, the guide wire comprising a stop configured to prevent movement of the guide wire in a direction opposite the first direction, and wherein the cannulation aperture has a smaller radius than a radius of the stop.

7. A bone plate assembly, comprising:

a plate having a plurality of apertures formed through the full thickness of the plate, with at least two of the plurality of apertures being positioned proximal to lateral edges on opposing sides of the plate;

one or more fasteners each having a first leading end, and a second end opposite the first leading end, each fastener being configured for the first leading end to pass substantially around a portion of bone and through at least one of the apertures for locking engagement to establish compression with adjustable tension between the plate and the bone;

a plurality of fastener attachments, each being incorporated with one of the apertures and configured to allow the first leading end of one of the fasteners to freely pass through one of the apertures in a first direction, and to resist fastener movement in a second direction opposite the first direction;

each fastener attachment comprising a base slot that accommodates entry of one of the fasteners first leading end into one of the fastener attachments to accept and secure the fastener, and an exit slot through which the fastener leading end exits the fastener attachment; and each fastener attachment comprising a toothed locking tab allowing the first leading end of one of the fasteners to pass freely in the first direction, wherein teeth of the locking tab are configured to press a portion of the respective fastener against a surface of the plate to resist movement of the fastener in the direction opposite the first direction.

8. The bone plate assembly of claim 7, wherein the one or more fasteners comprises at least two fasteners, each of which engages one of the fastener attachments incorporated with one of the apertures of the plate to provide tensioning at the first leading end, the second end, or both ends thereof for simultaneous tensioning and locking of each fastener through the respective fastener attachments on opposing sides of the plate.

9. The bone plate assembly of claim 7, wherein at least one of the fasteners further comprises a cannulation aperture and a cannulated core for receiving a guide wire that assists movement of the respective fastener in the first direction, the guide wire comprising a stop configured to prevent movement of the guide wire in a direction opposite the first direction, and wherein the cannulation aperture has a smaller radius than a radius of the stop.

\* \* \* \* \*

UNITED STATES PATENT AND TRADEMARK OFFICE
CERTIFICATE OF CORRECTION

PATENT NO. : 11,241,264 B2
APPLICATION NO. : 16/208707
DATED : February 8, 2022
INVENTOR(S) : Louis Houff It is certified that error appears in the above-identified patent and that said Letters Patent is hereby corrected as shown below:

In the Claims

In Claim 1, Column 25 Line 13, the following sentence should be inserted:
-- and an exit slot through which the fastener first leading end exits the fastener attachment --
after the word "attachment" and before the sentence "and wherein each fastener comprises ribs configured to engage an interior surface..."

Signed and Sealed this
Twelfth Day of September, 2023

*Katherine Kelly Vidal*

Katherine Kelly Vidal
*Director of the United States Patent and Trademark Office*